(12) United States Patent
Doshi et al.

(10) Patent No.: US 11,840,798 B2
(45) Date of Patent: Dec. 12, 2023

(54) CARBON NANOCOMPOSITE SENSORS

(71) Applicant: University of Delaware, Newark, DE (US)

(72) Inventors: Sagar Doshi, Newark, DE (US); Kaleb Burch, Newark, DE (US); Jill Higginson, Newark, DE (US); Erik Thostenson, Newark, DE (US); Amit Chaudhari, Newark, DE (US)

( * ) Notice: Subject to any disclaimer, the term of this patent is extended or adjusted under 35 U.S.C. 154(b) by 579 days.

(21) Appl. No.: 16/851,092

(22) Filed: Apr. 16, 2020

(65) Prior Publication Data

US 2021/0002816 A1    Jan. 7, 2021

Related U.S. Application Data

(60) Provisional application No. 62/834,422, filed on Apr. 16, 2019.

(51) Int. Cl.

| | |
|---|---|
| *D06M 11/74* | (2006.01) |
| *A43B 3/12* | (2006.01) |
| *A41D 1/00* | (2018.01) |
| *A43B 13/14* | (2006.01) |
| *G01L 1/18* | (2006.01) |
| *A61B 5/00* | (2006.01) |
| *A61B 5/11* | (2006.01) |
| *A61B 5/27* | (2021.01) |
| *B82Y 30/00* | (2011.01) |
| *B82Y 40/00* | (2011.01) |
| *G01L 1/20* | (2006.01) |
| *A43B 3/34* | (2022.01) |
| *D06M 101/38* | (2006.01) |

(Continued)

(52) U.S. Cl.
CPC .............. *D06M 11/74* (2013.01); *A41D 1/002* (2013.01); *A43B 3/128* (2013.01); *A43B 3/34* (2022.01); *A43B 13/14* (2013.01); *A61B 5/112* (2013.01); *A61B 5/27* (2021.01); *A61B 5/4528* (2013.01); *A61B 5/6807* (2013.01); *B82Y 30/00* (2013.01); *B82Y 40/00* (2013.01); *G01L 1/18* (2013.01); *G01L 1/205* (2013.01); *A61B 2562/0261* (2013.01); *D06M 2101/06* (2013.01); *D06M 2101/12* (2013.01); *D06M 2101/36* (2013.01); *D06M 2101/38* (2013.01)

(58) Field of Classification Search
CPC ....... G01L 1/18; B32B 5/26; B32B 2260/046; B82Y 30/00; B82Y 40/00; C08J 5/005; G01M 5/0033; G01M 5/0083
See application file for complete search history.

(56) References Cited

U.S. PATENT DOCUMENTS

| | | | | |
|---|---|---|---|---|
| 9,776,916 B2 * | 10/2017 | Thostenson | .......... | C09D 5/4419 |
| 2015/0044656 A1 * | 2/2015 | Eichhorn | ................ | A61B 5/11 |
| | | | | 600/587 |

OTHER PUBLICATIONS

Erik T. Thostenson and Tsu-Wei Chou, "Carbon nanotube networks: sensing of distributed strain and damage for life prediction and healing." Advanced Materials, Oct. 2, 2006, pp. 2837-2841, 8, WILEY-VCH Verlag GmbH & Co., Germany.

(Continued)

*Primary Examiner* — Lynda Salvatore
(74) *Attorney, Agent, or Firm* — RAMBERG IP, LLC

(57) ABSTRACT

A piezoresistive sensor featuring a fabric of woven or nonwoven fibers coated with carbon nanotubes can be integrated with footwear or clothing to serve as a pressure sensor that can monitor and/or analyze human activity during the course of the activities of daily living of the wearer.

11 Claims, 28 Drawing Sheets

(51) Int. Cl.
D06M 101/06 (2006.01)
D06M 101/12 (2006.01)
D06M 101/36 (2006.01)

(56) References Cited

OTHER PUBLICATIONS

Shafique Ahmed, Erik T. Thostenson, Thomas Schumacher, Sagar M. Doshi, Jennifer R. McConnell, "Integration of carbon nanotube sensing skins and carbon fiber composites for monitoring and structural repair of fatigue cracked metal structures." Composite Structures, Jul. 3, 2018, pp. 182-192, 203, Elsevier Ltd., Netherlands.

Shayamal Patel, Hyung Park, Paolo Bonato, Leighton Chan and Mary Rodgers, "A review of wearable sensors and systems with application in rehabilitation," Journal of NeuroEngineering and Rehabilitation, Apr. 20, 2012, pp. 1-17, 9:21, BioMed Central Ltd., United Kingdom.

Sungmook Jung, Ji Hoon Kim, Jaemin Kim, Suji Choi, Jongsu Lee, Inhyuk Park, Taeghwan Hyeon, and Dae-Hyeong Kim, "Reverse-Micelle-Induced Porous Pressure-Sensitive Rubber for Wearable Human-Machine Interfaces," Advanced Materials, May 15, 2014, pp. 4825-4830, 26, WILEY-VCH Verlag Gmbh & Co., Germany.

Xiangpeng Liang, Hadi Heidari, Ravinder Dahiya, "Wearable Capacitive-based Wrist-worn Gesture Sensing System", New generation of CAS, 2017, pp. 181-184, IEEE, United States.

Shafique Ahmed, Sagar Doshi, Thomas Schumacher, Erik T. Thostenson, and Jennifer McConnell, "Development of a novel integrated strengthening and sensing methodology for steel structures using CNT-based composites." Journal of Structural Engineering (2016) 04016202, 10 pp., 143(4), ASCE, Reston, VA, United States.

C.H. Hu, C.H. Liu, L.Z. Chen, Y.C. Peng, and S.S. Fan, "Resistance-pressure sensitivity and a mechanism study of multiwall carbon nanotube networks/poly (dimethylsiloxane) composites." Applied Physics Letters, Jul. 23, 2008, 033108, 4 pp., 93, American Institute of Physics, College Park, MD, United States.

Qi An, Andrew N. Rider, and Erik T. Thostenson, "Hierarchical composite structures prepared by electrophoretic deposition of carbon nanotubes onto glass fibers." ACS applied materials & interfaces, Feb. 4, 2013, 2022-2032, 5, American Chemical Society, Washington, DC, United States.

Takeo Yamada, Yuhei Hayamizu, Yuki Yamamoto, Yoshiki Yomogida, Ali Izadi-Najafabadi, Don N. Futaba, and Kenji Hata, "A stretchable carbon nanotube strain sensor for human-motion detection", Nature Nanotechnology, Mar. 27, 2011, pp. 296-301, 6, SpringerNature, London, United Kingdom.

Peter Gibbs and H. Harry Asada, "Wearable conductive fiber sensors for measuring joint movements." Proceedings of the IEEE International Conference on Robotics and Automation, Apr. 2004, pp. 4753-4758, vol. 5, IEEE, United States.

Corinne Mattmann, Frank Clemens and Gerhard Tröster, "Sensor for measuring strain in textile." Sensors, Jun. 3, 2008, pp. 3719-3732, 8, Multidisciplinary Publishing Institute, Basel, Switzerland.

Shayan Seyedin, Joselito M. Razal, Peter C. Innis, Ali Jeiranikhameneh, Stephen Beirne, and Gordon G. Wallace, "Knitted Strain Sensor Textiles of Highly Conductive All-Polymeric Fibers." ACS Applied Materials and Interfaces, Sep. 3, 2015, pp. 21150-21158, 7, American Chemical Society, Washington, DC, United States.

Ozgur Atalay, William Richard Kennon, and Muhammad Dawood Husain, "Textile-based weft knitted strain sensors: Effect of fabric parameters on sensor properties." Sensors, Aug. 21, 2013, pp. 11114-11127, 13, Multidisciplinary Publishing Institute, Basel, Switzerland.

Erik T. Thostenson, and Tsu-Wei Chou, "Carbon nanotube networks: Sensing of distributed strain and damage for life prediction and self healing." Advanced Materials, Oct. 2, 2006, pp. 2837-2841, 18, WILEY-VCH Verlag GmbH & Co., Germany.

Yi Li, X. Y. Cheng, M. Y. Leung, J. Tsang, X. M. Tao, and M. C. W. Yuen, "A flexible strain sensor from polypyrrole-coated fabrics." Synthetic metals, Oct. 10, 2005, pp. 89-94, 155, Elsevier Ltd., Netherlands.

Mohammad Ziabari Seyedin, Joselito M. Razal, Peter C. Innis, and Gordon G. Wallace, "Strain-Responsive polyurethane/PEDOT: PSS elastomeric composite Fibers with high electrical conductivity." Advanced Functional Materials, Feb. 18, 2014, pp. 2957-2966, 24, WILEY-VCH Verlag GGmbH & Co., Germany.

Jaechong Lee, Hyukho Kwon, Jungmok Seo, Sera Shin, Ja Hoon Koo, Changhyun Fang, Seungbae Son, Jae Hyung Kim, Yong Hoon Jang, Dae Eun Kim and Taeyoon Lee, "Conductive fiber based ultrasensitive textile pressure sensor for wearable electronics," Advanced materials, Feb. 18, 2015, pp. 2433-2439, 27, WILEY-VCH Verlag Gmbh & Co., Germany.

Shu Gong, Willem Schwalb, Yongwei Wang, Yi Chen, Yue Tang, Jye Si, Bijan Shirinzadeh & Wenlong Cheng, "A wearable and highly sensitive pressure sensor with ultrathin gold nanowires" Nature communications, Feb. 4, 2014, pp. 3132-3139, 5, Macmillan Publishers Limited, United Kingdom.

Tran Thanh Tung, MD J. Nine, Melinda Krebsz, Tibor Pasinszki, Campbell J. Coghlan, Diana N.H. Tran, and Dusan Losic, "Recent advances in sensing applications of graphene assemblies and their composites." Advanced Functional Materials, Oct. 20, 2017, pp. 1702891-1702948, 27, WILEY-VCH Verlag GmbH & Co., Germany.

Guangming Cai, Mengyun Yang, Zhenglin, Xu, Jiangang Liu, Bin Tang, and Xungai Wang, "Flexible and wearable strain sensing fabrics", Chem. Eng. J., May 15, 2017, p. 396-403, vol. 325, Elsevier Ltd., Netherlands.

Joseph T. Muth, Daniel M. Vogt, Ryan L. Truby, Tiğit Mengüç, David B. Kolesky, Robert J. Wood, and Jennifer A. Lewis, "Embedded 3D printing of strain sensors within highly stretchable elastomers", Adv. Mater., Jun. 16, 2014, p. 6307-6312, vol. 26, WILEY-VCH Verlag GmbH & Co., Germany.

Minxuan Xu, Junjie Qi, Feng Li, and Yue Zhang, "Highly stretchable strain sensors with reduced graphene oxide sensing liquids for wearable electronics", Nanoscale, Feb. 6, 2018, p. 5264-5271, vol. 10, The Royal Society of Chemistry, London, United Kingdom.

Xiao-Guang Yu, Yuan-Qing Li, Wei-Bin Zhu, Pei Huang, Tong-Tong Wang, Ning Hu, and Shao-Yun Fu, "A wearable strain sensor based on a carbonized nano-sponge/silicone composite for human motion detection", Nanoscale, Apr. 18, 2017, p. 6680-6685, vol. 9, The Royal Society of Chemistry, London, United Kingdom.

Yuan-Qing Li, Pei Huang, Wei-Bin Zhu, Shao-Yun Fu, Ning Hu, and Kin Liao, "Flexible wire-shaped strain sensor from cotton thread for human health and motion detection", Scientific Reports, Mar. 21, 2017, 7 pp., vol. 7, Springer Nature, United Kingdom.

Yuanqing Li, Yarjan Abdul Samad, and Kin Liao, "From cotton to wearable pressure sensor", Journal of Materials Chemistry A, Nov. 25, 2014, p. 2181-2187, vol. 3, The Royal Society of Chemistry, London, United Kingdom.

Biao Yin, Wanwei Wen, Tao Hong, Zhongshuai Xie, Guoliang Yuan, Qingmin Ji, and Hongbing Jia, "Highly Stretchable, Ultrasensitive, and Wearable Strain Sensors Based on Facilely Prepared Reduced Graphene Oxide Woven Fabrics in an Ethanol Flame", ACS Appl. Mater. Interfaces, Aug. 30, 2017, p. 32054-32064, vol. 9, American Chemical Society, Washington, DC, United States.

Nan Nan, Jianxin He, Xiaolu You, Xianqiang Sun, Yuman Zhou, Kun Qi, Weili Shao, Fan Liu, Yanyan Chu, and Bin Ding, "A Stretchable, Highly Sensitive, and Multimodal Mechanical Fabric Sensor Based on Electrospun Conductive Nanofiber Yarn for Wearable Electronics", Adv. Mater. Technol., Dec. 5, 2018, 11 pp., vol. 4, WILEY-VCH Verlag GmbH & Co., Germany.

Jonathan N. Coleman, Umar Khan, Werner J. Blau, and Yurii K. Gun'ko, "Small but strong: a review of the mechanical properties of carbon nanotube-polymer composites", Carbon, (2006), p. 1624-1652, vol. 44, No. 9, Elsevier Ltd., Netherlands.

Shafique Ahmed, Sagar Doshi, Thomas Schumacher, Erik T. Thostenson, and Jennifer McConnell, "Development of a novel integrated strengthening and sensing methodology for steel structures using CNT-

(56) References Cited

OTHER PUBLICATIONS based composites", *Journal of Structural Engineering*, Oct. 26, 2016, 10 pp., vol. 143, No. 4, American Society of Civil Engineering, Reston, VA, United States.

Shafique Ahmed, Erik T. Thostenson, Thomas Schumacher, Sagar M. Doshi, and Jennifer R. McConell, "Integration of carbon nanotube sensing skins and carbon fiber composites for monitoring and structural repair of fatigue cracked metal structures", *Composite Structures*, Jul. 3, 2018, p. 182-192, vol. 203, Elsevier Ltd., Netherlands.

Jaemin Kim, Mincheol Lee, Hyung Joon Shim, Roozbeh Ghaffari, Hye Rim Cho, Donghee Son, Yei Hwan Jung, Min Soh, Changsoon Choi, Sungmook Jung, Kon Chu, Daejong Jeon, Soon-Tae Lee, Ji Hoon Kim, Seung Hong Choi, Tadghwan Hyeon & Dae-Hyeong Kim, "Stretchable silicon nanoribbon electronics for skin prosthesis," Nature Communications, Dec. 9, 2014, pp. 1-11, 5:5747, Macmillan Publishers Limited, United Kingdom.

Xinqin Liao, Qingliang Liao, Zheng Zhang, Xiaoqin Yam, Qijie Liamg, Qimyu Wang, Minghua Li, and Yue Zhang, "A Highly Stretchable ZnO@Fiber-Based Multifunctional Nanosensor for Strain/Temperature/UV Detection", Advanced Functional Materials, Feb. 8, 2016, pp. 3074-3081, 26, WILEY-VCH Verlag Gmbh & Co., Germany.

Jun Wang, Jinting Jiu, Masaya Nogi, Tohru Sugahara, Shijo Nagao, Hirotaka Koga, Peng He and Katsuaki Suganuma, "A highly sensitive and flexible pressure sensor with electrodes and elastomeric interlayer containing silver nanowires," Nanoscale (2015), pp. 2926-2932, 7, The Royal Society of Chemistry, United Kingdom.

\* cited by examiner

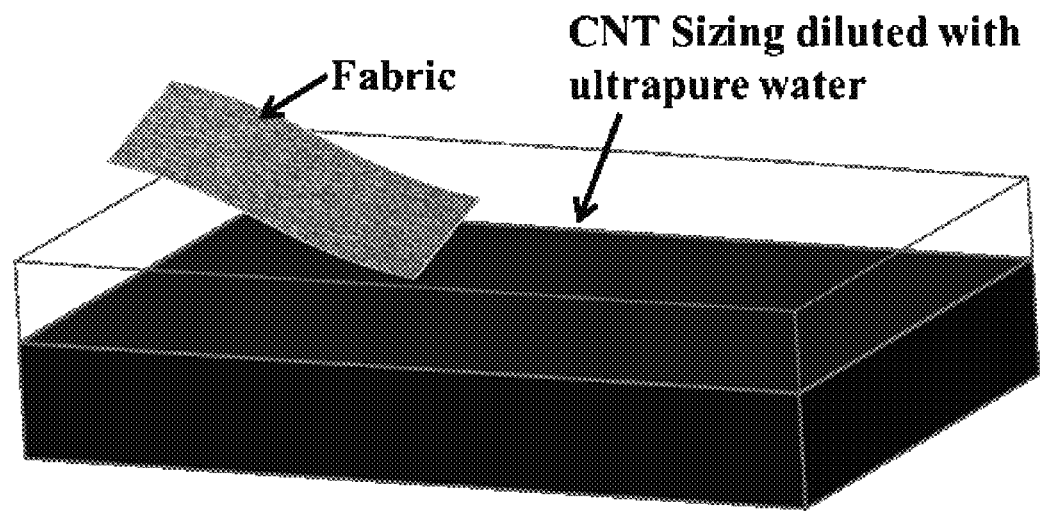
FIG. 7A
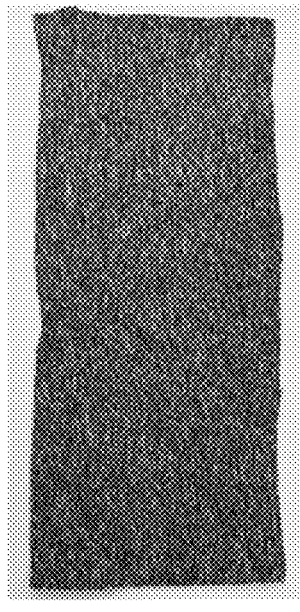 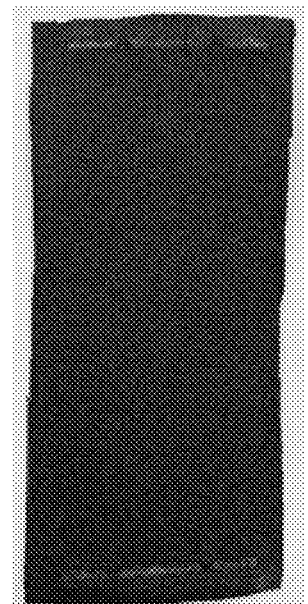
FIG. 7B          FIG. 7C

Before Coating
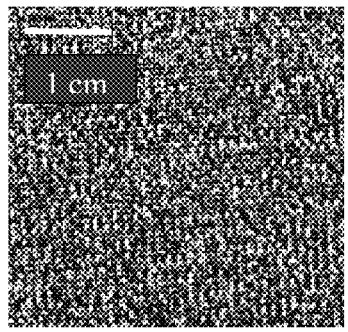
After Coating
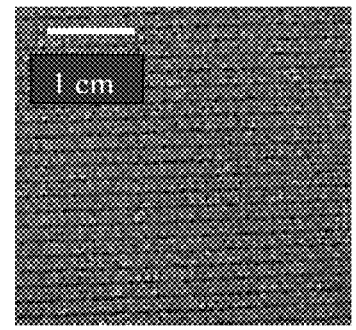
FIG. 14A
FIG. 14B
Before Coating
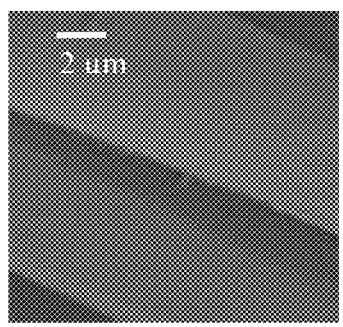
After Coating
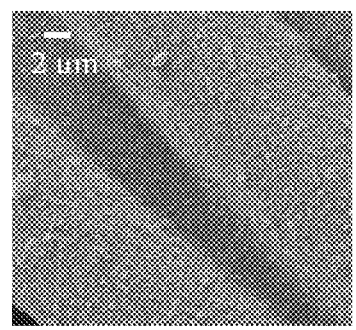
FIG. 14C
FIG. 14D

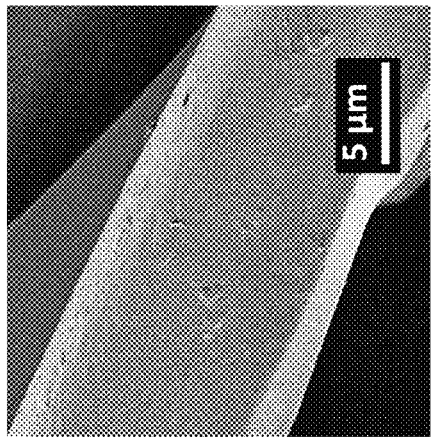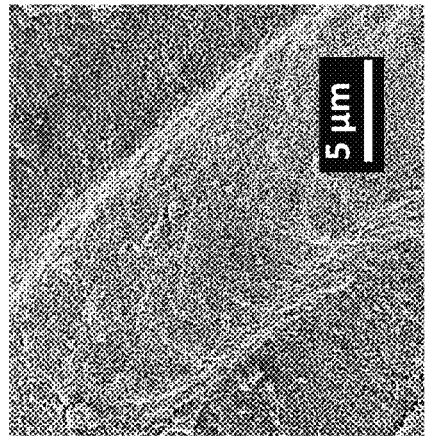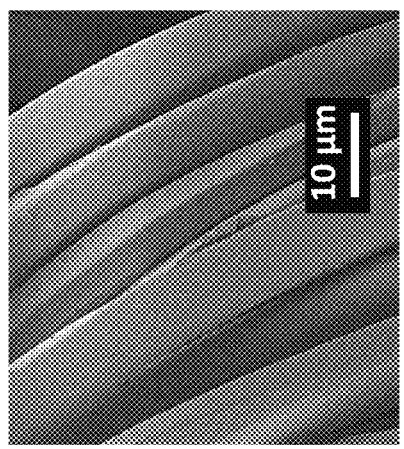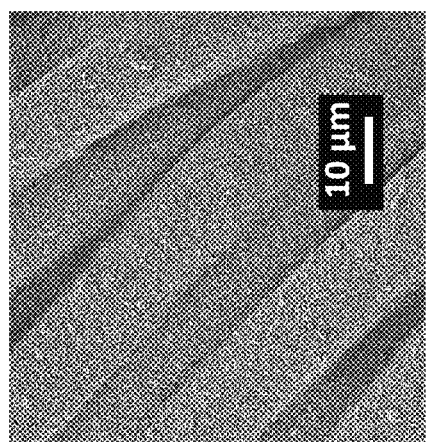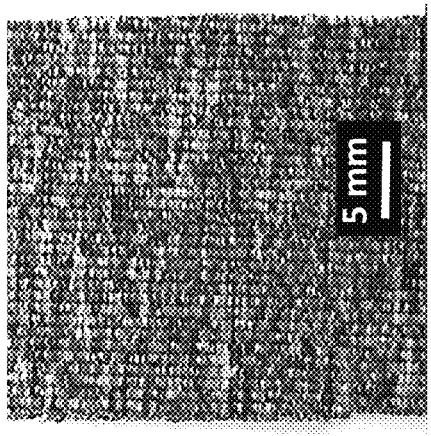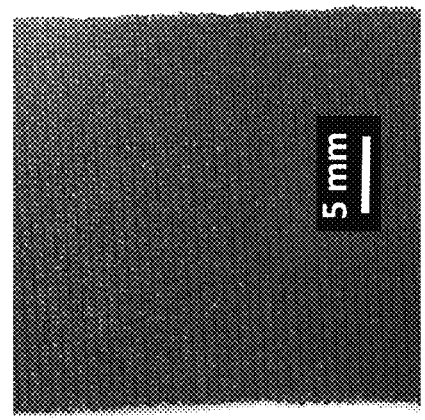
FIG. 19A
FIG. 19B

CARBON NANOCOMPOSITE SENSORS

CROSS-REFERENCE TO RELATED APPLICATION

This patent document claims the benefit of commonly owned U.S. Provisional Patent Application No. 62/462,344, filed Apr. 16, 2019. The entire contents of this provisional patent application are expressly incorporated by reference herein.

STATEMENT REGARDING FEDERALLY SPONSORED RESEARCH

This invention was made with government support under Grant No. DTFH31-13-H00010 awarded by the Federal Highway Administration. Acknowledgement is further made of support from the Delaware Idea Networks of Biomedical Research Excellence (INBRE) program with a grant from the National Institute of General Medical Sciences (NIGMS) Grant No. P20 GM103446), and the state of Delaware and the National Science Foundation (NSF) Grant No. 1254540. The United States Government has certain rights in the invention.

BACKGROUND OF THE INVENTION

1. Field of the Invention

The instant invention relates to piezoresistive sensors, and particularly those that may be integrated into footwear or articles of clothing for monitoring state(s) of human movement or motion.

2. Discussion of Related Art

Everything from automobiles to electrical appliances and manufacturing equipment is connected to the internet in today's world, with large amounts of data collected from a variety of conventional sensors. As people realize the advantages and importance of the information provided from data, there has been a tremendous interest in developing flexible and wearable sensors for collecting human physiological and movement data. These sensors have many versatile applications in robotics, performance monitoring in sports and athletics, health and rehabilitation monitoring, biomedical devices, electronic skins, flexible batteries, and entertainment using virtual reality.

The development of flexible pressure sensors is of great interest in recent years for applications in the field of human motion analysis [1], soft robotics [2], human-machine interfacing [3], gesture recognition [4], and orthotics/prosthetics [5]. Space constraints and weight limitations make the use of many conventional pressure sensors difficult for these applications. Pressure sensors developed recently leverage piezoelectric and triboelectric sensing mechanisms. Sensors based on piezoresistive and capacitive mechanisms are also being studied extensively.

A wide range of conductive materials such ZnO nanowires [6], silver nanowires [7] silver nanoparticles [8], gold nanowires [9] and graphene [10] have been investigated to tailor and optimize the sensitivity and range of pressure measurement. Nanocarbon materials, such as graphene, carbon nanotubes and carbon nanofibers have also been examined for sensors due to their high electrical conductivity. Carbon nanotubes, in particular, are suitable candidates for creating flexible pressure sensors and electronics because of their mechanical flexibility, electrical conductivity and intrinsic carrier mobility. Nanotubes have been investigated for strain and damage sensing in composites as well as structural health monitoring of civil infrastructure [11-15], and they have been added to elastomers such as PDMS to create stretchable sensors [16]. An alternate approach to mixing carbon nanotubes in polymers is grafting them directly onto fibers or textiles. Carbon nanotubes have been grafted onto glass fibers for composites [17].

Human motion analysis, in particular, is a subject of interest for the last two decades among physical therapists and sports science researchers. Human motion is typically studied in a laboratory setting. The most commonly used technique involves the use of motion capture cameras along with fixing markers attached to the body for tracking. Although these techniques are commonly used in a research environment, there are many limitations of utilizing laboratory-based systems for monitoring human motion. Aside from being expensive, the laboratory conditions are very different from daily home/work environments, and patients are not monitored during their day-to-day activities. Additionally, patients can only be monitored for a limited amount of time. Furthermore, the instrumentation using markers and data analysis is complex.

An alternative approach is wearable sensors integrated into garments that are flexible and stretchable. Drapability of fabrics—the ability to conform to any shape—makes them suitable for flexible sensors that can be integrated into garments or directly attached to the skin.

Considering the difficulties faced in developing stretchable electrical conductive materials, instead of developing new materials, researchers have proposed unique structural combinations from existing materials. [18] One of the initial solutions proposed by Gibbs et al. [19] is to incorporate inelastic metallic wire in the fabric to measure the resistance across variable contact length on joint motion. Mattmann and co-workers [20] developed a strain-sensitive conductive fiber with a mixture of a thermoplastic elastomer and carbon black particles and were able to recognize upper body postures with an accuracy of 97%. Similarly, others have developed knitted strain sensor textiles of conductive polymeric fibers [21]. Atalay et al. [22] developed a knitted strain sensor using silver-coated fibers. While metallic coatings give promising results, the coatings increase the stiffness of the fabric making it less comfortable.

Additionally, the metallic coating often cracks under high deformation and can be prone to corrosion. Therefore, researchers have investigated specialized conductive polymers such as polypyrrole [24] and PEDOT [25] to create electrically conductive fabrics. Alternatively, some approaches use carbon black [26], reduced graphene oxide [27] or gold/silver nanoparticles [28 29], and carbon nanotubes [30] to produce flexible sensors.

Further, researchers have investigated the use of carbon nanotubes (CNTs) to create flexible sensors. The coupling of electrical and mechanical properties makes CNTs a suitable candidate for developing sensors. High aspect ratio CNTs form a conductive percolating network. [23] Yamada et al. [18] introduced a stretchable sensor consisting of aligned single-walled CNT thin films deposited on polydimethylsiloxane resulting in a flexible sensor capable of measuring high strain. Over the past several years the cost of CNTs has come down considerably, making them a viable material for the development of low-cost wearable sensors.

The ability to measure the movement of a body part or a particular joint creates the opportunity to provide feedback or intervention to improve mobility or prevent injury. As a result, the interest in developing flexible wearable, sensors has increased significantly in recent years.

One of the most significant differences in developing wearable sensors for human motion analysis when compared to sensors for structural health monitoring is the need for flexibility along with soft texture. User comfort and non-invasiveness, along with sensitivity, are critical factors to consider for wearable sensors, especially when they are expected to be worn by people over long time periods.

Human gait analysis and joint movement data is conventionally collected in a laboratory setup with instrumented treadmill and motion capture cameras. While these techniques are well established and highly effective in the analysis of human motion, there are many limitations and challenges in utilizing laboratory-based measurements for wide-scale use in rehabilitation monitoring and behavior modification and learning. Firstly, this equipment is extremely expensive, complicated to use, and not readily available in a home or community setting. Additionally, it is difficult to monitor patients over long time intervals in the laboratory setting, and lastly, the patients are not monitored during their day-to-day activities. The ability to monitor a specific joint or limb using non-invasive wearable sensors creates an opportunity to provide feedback or intervention to enhance the function and improve quality of life.

Unlike a typical metallic strain gage where the resistance changes due to dimensional changes, piezoresistive flexible wearable sensors have been developed using different nanomaterials and innovative micro/nanostructures. For resistive wearable sensors, the change in resistance is mainly due to the tunneling effect between conductive particles and the disconnection of contact points between conductive reinforcements.

Mixing of electrically conductive active materials with polymers such as polydimethylsiloxane (PDMS) to create flexible sensors is commonly used due to the ease of manufacturing, low cost and flexibility. Commonly used fillers as the conductive additive in elastomers are carbon black, graphene, carbon nanotubes, and metallic powder. However, hysteresis, low stretchability, and user comfort are challenges that remain to be addressed. Additionally, the stiffening and aging of elastomers due to water absorption pose a challenge making them brittle. Lastly, integrating these sensors with clothing without affecting the texture and breathability is difficult.

Flexible sensors have also been developed using many different approaches such as using carbon nanotubes and silver nanowire in self-healing hydrogel [31], skin inspired double-layer hydrogels [32], spray coating of carbon nanotubes on Ecoflex [33], wet spinning of silver nanowires and silver nanoparticles in styrene-butadiene-styrene elastomeric matrix [34]. Researchers have also used coaxial wet spinning of carbon nanotube-based core-sheath fiber protected by silicone elastomer [35], silver nanoparticle thin film patterned on PDMS using a one-step direct transfer process [36], dip coating of graphene oxide nanosheets followed by the reduction using sodium borohydride [37], embedded 3D printing of carbon black based ink in a modified Ecoflex reservoir [38], and reduced graphene oxide sensing liquid filled in Ecoflex rubber [39]. Various techniques have been used to make conductive fabrics which are then encapsulated in flexible elastomers such as carbonization of a nano-sponge followed by encapsulation with silicone resin [40], carbonizing cotton threads in nitrogen and then using PDMS [41], high temperature pyrolysis of commonly available tissue paper to make a carbon paper and using it with PDMS elastomer as the flexible substrate [42] and pyrolyzing commercial cotton bandages coated with graphene oxide in ethanol flame and embedding them in natural rubber latex [43]. Fabric-based wearable sensors have also shown promise due to the ease of integration and the potentially higher user comfort. Nan et al. [44] used electrospinning to prepare graphene oxide doped polyacrylonitrile nanofiber yarns, which were then coated with conductive polypyrrole and then wound on elastic yarns before weaving into a fabric-like sensor. Industrial application of these wearable sensors remains a challenge due to complicated manufacturing, compatibility with existing production techniques in the textile industry, and seamless, non-invasive integration into garments that are worn commonly. Therefore, a critical need still exists for developing cost effective, stretchable, and flexible wearable sensors with high sensitivity and user comfort.

3. Commonly Owned Art

Due to their excellent mechanical and electrical properties, carbon nanotubes have been widely studied for creating hierarchical composites with improved mechanical properties [45] or self-sensing capabilities [46]. Carbon nanotubes have also been deposited on non-woven fabrics to create sensing skins for structural health monitoring of civil infrastructure [47,48]

4. References

1. Patel, Shyamal, et al. "A review of wearable sensors and systems with application in rehabilitation." *Journal of neuroengineering and rehabilitation* 9.1 (2012): 21. Trivedi, doi.org/10.1186/1743-0003-9-21
2. Trivedi, Deepak, et al. "Soft robotics: Biological inspiration, state of the art, and future research." *Applied bionics and biomechanics* 5.3 (2008): 99-117.dx.doi.org/10.1080/11762320802557865
3. Jung, Sungmook, et al. "Reverse micelle induced porous pressure sensitive rubber for wearable human-machine interfaces." *Advanced Materials* 26.28 (2014): 4825-4830. doi.org/10.1002/adma.201401364
4. Liang, Xiangpeng, Hadi Heidari, and Ravinder Dahiya. "Wearable Capacitive-Based Wrist-Worn Gesture Sensing System." CAS (NGCAS), 2017 *New Generation of*. IEEE, 2017. 10.1109/NGCAS.2017.80
5. Kim, Jaemin, et al. "Stretchable silicon nanoribbon electronics for skin prosthesis." *Nature communications* 5 (2014): 5747. 10.1038/ncomms6747 (2014)
6. Liao, Xinqin, et al. "A Highly Stretchable ZnO@ Fiber Based Multifunctional Nanosensor for Strain/Temperature/UV Detection." *Advanced Functional Materials* 26.18 (2016): 3074-3081. doi.org/10.1002/adfm.201505223
7. Wang, Jun, et al. "A highly sensitive and flexible pressure sensor with electrodes and elastomeric interlayer containing silver nanowires." *Nanoscale* 7.7 (2015): 2926-2932. 10.1039/C4NR06494A
8. Lee, Jaehong, et al. "Conductive fiber based ultrasensitive textile pressure sensor for wearable electronics." *Advanced materials* 27.15 (2015): 2433-2439. doi.org/10.1002/adma.201500009
9. Gong, Shu, et al. "A wearable and highly sensitive pressure sensor with ultrathin gold nanowires." *Nature communications* 5 (2014): 3132. 10.1038/ncomms4132 (2014)
10. Tung, Tran Thanh, et al. "Recent advances in sensing applications of graphene assemblies and their composites." Advanced Functional Materials 27.46 (2017): 1702891. doi.org/10.1002/adfm.201702891

11. Thostenson, Erik T., and T. W. Chou. "Carbon nanotube networks: sensing of distributed strain and damage for life prediction and healing." *Advanced Materials* 18.21 (2006): 2837-2841. doi.org/10.1002/adma.200600977

12. Ahmed, Shafique, et al. "Integration of carbon nanotube sensing skins and carbon fiber composites for monitoring and structural repair of fatigue cracked metal structures." Composite Structures 203 (2018): 182-192. doi.org/10.1016/j.compstruct.2018.07.005

13. Ahmed, Shafique, et al. "Development of a novel integrated strengthening and sensing methodology for steel structures using CNT-based composites." *Journal of Structural Engineering* 143.4 (2016): 04016202. doi.org/10.1061/(ASCE)ST.1943-541X.0001697

14. Doshi, Sagar M., and Thostenson, Erik T. "Novel Carbon Nanotube-Based Non-Woven Composite Sensors: Processing, Characterization and Potential Applications." *Proceedings of the American Society for Composites: Thirty-First Technical Conference.* 2016. www.dpi-proceedings. com/index.php/asc31/article/view/3183

15. Doshi Sagar M. and Thostenson Erik T. "Self-sensing carbon nanotube composites: processing and characterization" ed K Friedrich and U Breuer Multifunctionality of Polymer Composites (Amsterdam: Elsevier). 2015. doi.org/10.1016/C2013-0-13006-1

16. Hu, C. H., et al. "Resistance-pressure sensitivity and a mechanism study of multiwall carbon nanotube networks/poly (dimethylsiloxane) composites." *Applied Physics Letters* 93.3 (2008): 033108. doi.org/10.1063/1.2961028

17. An, Qi, Andrew N. Rider, and Erik T. Thostenson. "Hierarchical composite structures prepared by electrophoretic deposition of carbon nanotubes onto glass fibers." ACS applied materials & interfaces 5.6 (2013): 2022-2032. 10.1021/am3028734

[18] Yamada, T., Hayamizu, Y., Yamamoto, Y., Yomogida, Y., Izadi-Najafabadi, A., Futaba, D. N. & Hata, K., "A stretchable carbon nanotube strain sensor for human-motion detection." Nature Nanotechnology vol. 6, no. 5 pp. 296-301 (2011). https://doi.org/10.1038/nnano 2011.36

[19] Gibbs, P., & Asada, H. H., "Wearable conductive fiber sensors for measuring joint movements." IEEE International Conference on Robotics and Automation, 2004. Proceedings. ICRA '04. 2004 no. April p. 4753-4758 Vol. 5 (2004). https://doi.org/10.1109/ROBOT.2004.1302469>

[20] Mattmann, C., Clemens, F. & Troster, G., "Sensor for measuring strain in textile." Sensors vol. 8, no. 6 pp. 3719-3732 (2008). https://doi.org/10.3390/s8063719

[21] Seyedin, S., Razal, J. M., Innis, P. C., Jeiranikhameneh, A., Beirne, S. & Wallace, G. G., "Knitted Strain Sensor Textiles of Highly Conductive All-Polymeric Fibers." ACS Applied Materials and Interfaces vol. 7, no. 38 pp. 21150-21158 (2015). https://doi.org/10.1021/acsami.5b04892

[22] Atalay, O., Richard Kennon, W. & Dawood Husain, M., "Textile-based weft knitted strain sensors: Effect of fabric parameters on sensor properties." Sensors (Switzerland) vol. 13, no. 8 pp. 11114-11127 (2013). https://doi.org/10.3390/s130811114

[23] Thostenson, E. T., & Chou, T. W., "Carbon nanotube networks: Sensing of distributed strain and damage for life prediction and self healing." Advanced Materials vol. 18, no. 21 pp. 2837-2841 (2006). https://doi.org/10.1002/adma.200600977

[24] Li, Yi, X. Y. Cheng, M. Y. Leung, J. Tsang, X. M. Tao, and M. C. W. Yuen. "A flexible strain sensor from polypyrrole-coated fabrics." Synthetic metals 155, no. 1 (2005): 89-94.

[25] Seyedin, Mohammad Ziabari, Joselito M. Razal, Peter C Innis, and Gordon G. Wallace. "Strain—responsive polyurethane/PEDOT: PSS elastomeric composite Fibers with high electrical conductivity." Advanced Functional Materials 24, no. 20 (2014): 2957-2966.

[26] Wu, Xiaodong, Yangyang Han, Xinxing Zhang, Zehang Zhou, and Canhui Lu. "Large-area compliant, low-cost, and versatile pressure sensing platform based on microcrack-designed carbon black@ polyurethane sponge for human-machine interfacing." Advanced Functional Materials 26, no. 34 (2016): 6246-6256.

[27] Yang, Zhen, Yu Pang, Xiao-lin Han, Yifan Yang, Jiang Ling, Muqiang Jian, Yingying Zhang, Yi Yang, and Tian-Ling Ren. "Graphene textile strain sensor with negative resistance variation for human motion detection." ACS nano 12, no. 9 (2018): 9134-9141.

[28] Maheshwari, Vivek, and Ravi F. Saraf. "High-resolution thin-film device to sense texture by touch." Science 312, no. 5779 (2006): 1501-1504.

[29] Lee, Jaehwan, Sanghyeok Kim, Jinjae Lee, Daejong Yang, Byong Chon Park, Seunghwa Ryu, and Inkyu Park. "A stretchable strain sensor based on a metal nanoparticle thin film for human motion detection." Nanoscale 6, no. 20 (2014): 11932-11939.

[30] Yamada, Takeo, Yuhei Hayamizu, Yuki Yamamoto, Yoshiki Yomogida, Ali Izadi-Najafabadi, Don N. Futaba, and Kenji Hata. "A stretchable carbon nanotube strain sensor for human-motion detection." *Nature nanotechnology* 6, no. 5 (2011): 296.

[31] G. Cai, J. Wang, K. Qian, J. Chen, S. Li, P. S. Lee, Extremely Stretchable Strain Sensors Based on Conductive Self-Healing Dynamic Cross-Links Hydrogels for Human-Motion Detection, Adv. Sci. 4 (2017). https://doi.org/10.1002/advs.201600190.

[32] Q. Zhang, X. Liu, L. Duan, G. Gao, Ultra-stretchable wearable strain sensors based on skin-inspired adhesive, tough and conductive hydrogels, Chem. Eng. J. 365 (2019) 10-19. https://doi. org/10.1016/j.cej.2019.02.014.

[33] M. Amjadi, Y. J. Yoon, I. Park, Ultra-stretchable and skin-mountable strain sensors using carbon nanotubes-Ecoflex nanocomposites, Nanotechnology. 26 (2015). https://doi.org/10.1088/0957-4484/26/37/375501.

[34] S. Lee, S. Shin, S. Lee, J. Seo, J. Lee, S. Son, H. J. Cho, H. Algadi, S. Al-Sayari, D. E. Kim, T. Lee, Ag nanowire reinforced highly stretchable conductive fibers for wearable electronics, Adv. Funct. Mater. 25 (2015) 3114-3121. https://doi.org/10.1002/adfm.201500628.

[35] Z. Tang, S. Jia, F. Wang, C. Bian, Y. Chen, Y. Wang, B. Li, Highly Stretchable Core-Sheath Fibers via Wet-Spinning for Wearable Strain Sensors, ACS Appl. Mater. Interfaces. 10 (2018) 6624-6635. https://doi.org/10.1021/acsami.7b18677.

[36] J. J. Lee, S. Kim, J. J. Lee, D. Yang, B. C. Park, S. Ryu, I. Park, A stretchable strain sensor based on a metal nanoparticle thin film for human motion detection, Nanoscale. 6 (2014) 11932-11939. https://doi.org/10.1039/c4nr03295k.

[37] G. Cai, M. Yang, Z. Xu, J. Liu, B. Tang, X. Wang, Flexible and wearable strain sensing fabrics, Chem. Eng. J. 325 (2017) 396-403. https://doi.org/10.1016/j.cej.2017.05.091.

[38] J. T. Muth, D. M. Vogt, R. L. Truby, Y. Mengüç, D. B. Kolesky, R. J. Wood, J. A. Lewis, Embedded 3D printing of strain sensors within highly stretchable elastomers, Adv. Mater. 26 (2014) 6307-6312. https://doi.org/10.1002/adma.201400334.
[39] M. Xu, J. Qi, F. Li, Y. Zhang, Highly stretchable strain sensors with reduced graphene oxide sensing liquids for wearable electronics, Nanoscale. 10 (2018) 5264-5271. https://doi.org/10.1039/c7nr09022f.
[40] X. G. Yu, Y. Q. Li, W. Bin Zhu, P. Huang, T. T. Wang, N. Hu, S. Y. Fu, A wearable strain sensor based on a carbonized nano-sponge/silicone composite for human motion detection, Nanoscale. 9 (2017) 6680-6685. https://doi.org/10.1039/c7nr01011g.
[41] Y. Q. Li, P. Huang, W. Bin Zhu, S. Y. Fu, N. Hu, K. Liao, Flexible wire-shaped strain sensor from cotton thread for human health and motion detection, Sci. Rep. 7 (2017) 1-7. https://doi.org/10.1038/srep45013.
[42] Y. Li, Y. A. Samad, K. Liao, From cotton to wearable pressure sensor, J. Mater. Chem. A. 3 (2015) 2181-2187. https://doi.org/10.1039/c4ta05810k.
[43] B. Yin, Y. Wen, T. Hong, Z. Xie, G. Yuan, Q. Ji, H. Jia, Highly Stretchable, Ultrasensitive, and Wearable Strain Sensors Based on Facilely Prepared Reduced Graphene Oxide Woven Fabrics in an Ethanol Flame, ACS Appl. Mater. Interfaces. 9 (2017) 32054-32064. https://doi.org/10.1021/acsami.7b09652.
[44] N. Nan, J. He, X. You, X. Sun, Y. Zhou, K. Qi, W. Shao, F. Liu, Y. Chu, B. Ding, A Stretchable, Highly Sensitive, and Multimodal Mechanical Fabric Sensor Based on Electrospun Conductive Nanofiber Yarn for Wearable Electronics, Adv. Mater. Technol. 4 (2019) 1-11. https://doi.org/10.1002/admt.201800338.
[45] Coleman, Jonathan N., Umar Khan, Werner J. Blau, and Yurii K. Gun'ko. "Small but strong: a review of the mechanical properties of carbon nanotube-polymer composites." Carbon 44, no. 9 (2006): 1624-1652.
[46] Doshi, Sagar M. and Erik T. Thostenson. "Self-sensing carbon nanotube composites: processing and characterization" ed K Friedrich and U Breuer Multifunctionality of Polymer Composites (Amsterdam: Elsevier) (2015) 752-784
[47] Ahmed, Shafique, Sagar Doshi, Thomas Schumacher, Erik T. Thostenson, and Jennifer McConnell. "Development of a novel integrated strengthening and sensing methodology for steel structures using CNT-based composites." Journal of Structural Engineering 143, no. 4 (2016): 04016202.
[48] Ahmed, Shafique, Erik T. Thostenson, Thomas Schumacher, Sagar M. Doshi, and Jennifer R. McConnell. "Integration of carbon nanotube sensing skins and carbon fiber composites for monitoring and structural repair of fatigue cracked metal structures." Composite Structures 203 (2018): 182-192.

SUMMARY OF THE INVENTION

In accordance with the instant invention, a piezoresistive sensor featuring a fabric of woven or nonwoven fibers coated with carbon nanotubes can be integrated with footwear or clothing to serve as a pressure sensor that can monitor and/or analyze human activity during the course of the activities of daily living of the wearer.

BRIEF DESCRIPTION OF THE FIGURES

FIG. 7A: Dip coating of fabric in CNT-sizing; FIG. 7B: Fabric before coating; FIG. 7C: Fabric after coating with CNT

FIGS. 14A-14D: Photographs of a (FIG. 14A) non-coated fabric, and (FIG. 14B) coated fabric, and scanning electron micrographs of (FIG. 14C) non-coated fabric and (FIG. 14D) coated fabric FIGS. 19A-19E: Photograph and scanning electron micrographs of the knitted fabric used for characterization (FIG. 19A) without carbon nanotube coating and (FIG. 19B) with carbon nanotube coating. FIG. 19C and FIG. 19D: the flexibility of the fabric after coating. FIG. 19E: cross-section of fiber within the fabric showing a porous and uniform coating of carbon nanotubes around the fiber

FIG. 25A shows the sensing response when writing the word "DELAWARE'. The sensor is extremely sensitive to be able to capture small finger movements due to writing. FIGS. 25B and 25C show the sensing response when writing the letter 'A,' the $4^{th}$ and $6^{th}$ letter. The sensing response is similar. This enables potential applications in gesture recognition and human-computer interaction.

DETAILED DESCRIPTION OF EMBODIMENTS OF THE INVENTION

Figure 1:
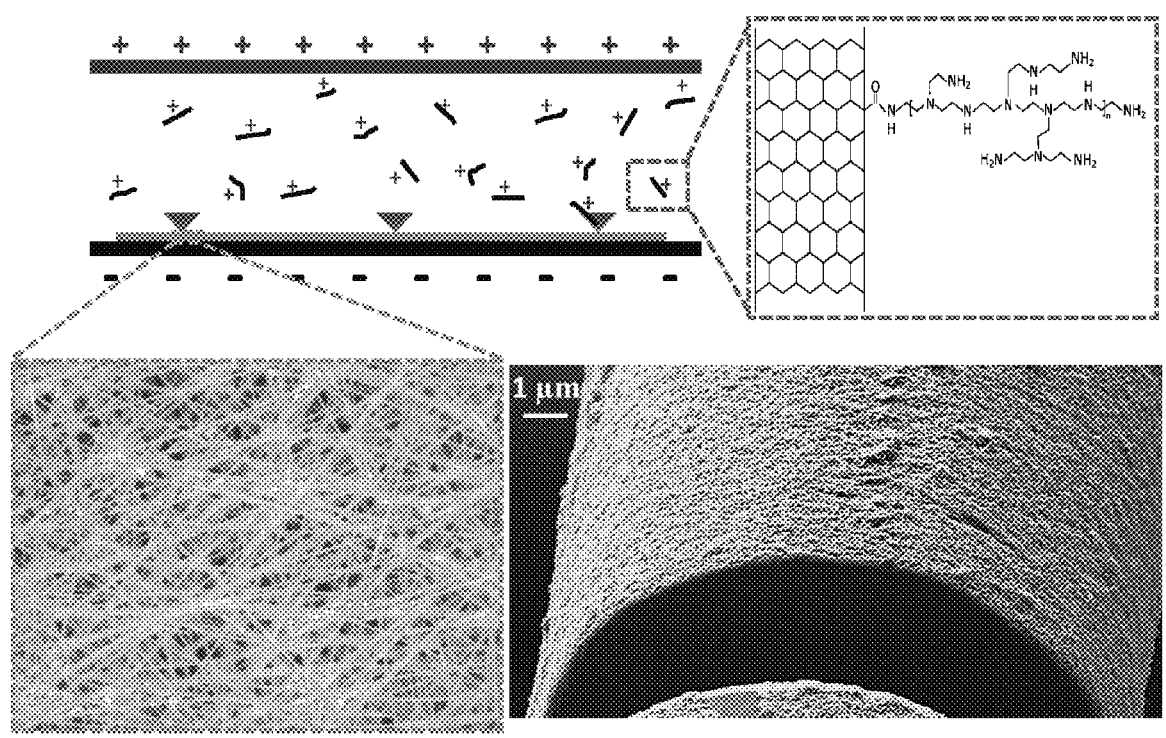
FIG. 1: (upper left) A schematic diagram of the EPD process to deposit functionalized carbon nanotubes on non-woven aramid fabric. (upper right) An illustration of a carbon nanotube functionalized with polyethylenimine (lower left) A picture of the non-woven aramid fabric taken using an optical microscope. (lower right) SEM micrograph of an aramid fiber cross-sectioned using Focused Ion Beam (FIB) showing a uniform coating of carbon nanotubes FIG. 2A Resistance response of Aramid-CNT specimen when loaded to 40 MPa followed by unloading.

In accordance with the instant invention, a piezoresistive sensor featuring a fabric of woven or nonwoven fibers coated with carbon nanotubes can be integrated with footwear or clothing to serve as a pressure sensor that can monitor and/or analyze human activity during the course of the activities of daily living of the wearer.

The instant invention encompasses, but is not necessarily limited to, a number of aspects. What the various aspects have in common is the deposition or coating of carbon nanotubes onto fibers in sufficient numbers and concentration as to create an electrically conductive coated fabric, the carbon nanotubes being electrically conductive. In one embodiment, the fabric is not inherently electrically conductive in the absence of the coated/deposited carbon nanotubes. At least two electrodes are then applied or positionally identified on the CNT-coated fabric, thereby defining electrical resistance between any two of the at least two electrodes. The electrodes are then electrically connected to an instrument or other means for measuring the electrical resistance, such as an ohm meter.

The CNT-coated fabric experiences changes in its electrical resistance in response to different stress states, and the deformation due to it; thus, making it useful as a sensor to sense such stress states. In other words, it is "piezoresistive". In one embodiment, the electrical resistance decreases when compressed. In another embodiment, the electrical resistance increases under the influence of a tensile force, or when an out-of-plane force is applied to a flexible, CNT-coated fabric.

The fabric that is coated to make a piezoresistive sensor features a collection of fibers that may be woven or not (i.e., nonwoven). Fibers may be organized as bundles or wound together to form a yarn. Among woven fabrics, there are many ways of organizing fibers, bundles or yarns into two-dimensionally repeating patterns (e.g., stitches), including fibers arranged in a plurality of loops (a looped structure) that repeats in two-dimensions, and may be interconnected or interlocked in two dimensions. Compositionally, the fibers making up a fabric may be natural fibers such as cotton, wool and silk, or may be synthetic such as nylon, rayon, glass, aramid, polyester, polyurethane and spandex.

Carbon nanotubes are coated or deposited onto the fabric by coating or depositing them onto the fibers making up the fabric. The coating may or may not be uniform throughout the thickness of the fabric; however, it is generally desired that the nanotubes be strongly or firmly bonded to the fibers of the fabric. To that end, the nanotubes may be "functionalized" with a polymer such as polyethyleneimine (PEI) to assist in this regard. Also helpful here is to slightly oxidize the exposed surface of the nanotubes by exposing the nanotubes to ozone gas ($O_3$), called "ozonolysis". The functionalizing process may apply an electrical charge such as a positive charge, to the carbon nanotubes. The positively charged nanotubes can then be pulled toward a negative charge such as a negatively charged electrode, using the electrostatic attraction force. This can be accomplished when the coating process takes place in a liquid bath. The fabric is placed at the bottom of a bath of aqueous solution. The functionalized nanotubes are placed in the bath, or may be functionalized while in the bath. An electric field may then be applied across the bath, with the negative electrode located at or behind the fabric at the bottom of the bath. The positively charged nanotubes will then be attracted into the fabric. Alternatively, the bath may be positively charged by protonating it, simply be reducing its pH below 7 (neutrality).

The nanotube coating on the fibers of the fabric is quite thin, typically less than 10 microns, more typically no more than 2 or 3 microns, often no more than about 1 micron in thickness, and an exemplary range may be about 250 to 750 nanometers (nm) in thickness. This thin coating may have a profound effect on the electrical resistance of the fabric, but it hardly changes the flexibility or drapability of the fabric. "Drapability" refers to the ability of the fabric to conform to a surface when it is placed in contact with that surface. Further, the coating hardly changes the porosity, the "openness" of the fabric, which has important consequences for the "breathability" of the fabric: it hardly changes the fabric's breathability.

The piezoresistive sensor may be used by itself, but more commonly it is integrated with another article such as another fabric. The other fabric may include a garment or other article of clothing, or an accessory thereto such as a hat or glove or article of footwear such as a sandal or shoe or boot. The integration of the piezoresistive sensor to the other fabric may be by most any known means, including stitching, gluing, heat fusing or heat bonding, etc. Since the piezoresistive sensor also includes a fabric, it may be useful to refer to the fabric of the sensor as the "first fabric" and the "other" fabric (to which the sensor is attached) as the "second fabric". The first and second fabrics may be identical in composition or not.

The garment that includes the instant piezoresistive sensor, sometimes referred to as a "smart garment" or a "wearable", may include a sleeve configured to fit around an extremity of a living being such as a human being, and specifically around an arm, including a wrist, a finger or thumb, or a leg, including an ankle. The sleeve is configured for a snug, compression fit, but not uncomfortably so. Thus, the sleeve could be integrated into a shirt, a glove, or a pair of pants. The sleeve could also be configured, for example, as to size and shape, to fit other mammals such as dogs, cats and horses.

In another embodiment, the piezoresistive sensor could be integrated into footwear such as a shoe or sandal, for example, into the sole of the footwear. For example, multiple sensors could be integrated into different portions of the sole, for example, the hindfoot (e.g., the heel), the forefoot (e.g., the toes), or the midfoot (e.g., the arch). Alternatively, a single sensor containing multiple electrodes could cover a large area of the sole and thus monitor compression stresses at different points in the sole. Further, a sensor of the instant invention mounted in a sidewall of a shoe could monitor stresses that the foot is exerting against the sidewall.

In a first aspect of the present invention, we discuss a scalable electrophoretic deposition (EPD) method of manufacturing carbon nanotube coated fabric-based flexible pressure sensors. A uniform coating of a nanocomposite comprising of polyethylenimine (PET) functionalized carbon nanotube is deposited on the surface of aramid fibers, which imparts the electrical conductivity and the piezoresistive sensing functionality to the fabric. These sensors have an extremely wide range of pressure sensing, from tactile pressures to body weight and even higher. Sensors are then integrated with footwear and investigated for potential applications in the analysis of human gait. The sensor response is validated using a treadmill instrumented with force sensors.

In a second aspect of the instant invention, we demonstrate the fabrication of highly sensitive, comfortable to wear sensors to measure a range of human joint motion. A dip-coating technique is developed to produce a thin nanocomposite coating on a commercially-available knitted fabric. The morphology of the coating is characterized using electron microscopy and the electrical-mechanical response characterized under tension. The fabric sensor is then integrated into an elbow sleeve and the sensing response under elbow motion is investigated.

In a third aspect of the invention, we demonstrate a novel processing technique to create thin conductive films of carbon nanotubes on knitted fabrics to create flexible stretch sensors which are breathable, light-weight, and comfortable to wear. The carbon nanotubes are chemically functionalized and deposited using an electric field from a water-based dispersion at room temperature. The carbon nanotube coating is studied using scanning electron microscopy, and the sensing response is characterized using simultaneous mechanical and electrical characterization. Proof-of-concept for using these sensors to detect human motion detection is demonstrated by integrating the sensors in knee sleeves and measuring the sensing response with knee flexion.

In a fourth aspect of the invention, an alternate embodiment of the third aspect of the invention, a comfortable to wear, flexible wearable sensor with ultra-high sensitivity using commercially available fabrics is demonstrated. An efficient electrophoretic deposition technique (discussed in Example 1) is used to create a conductive nanostructured composite coating on fabrics such as polyester, rayon, wool and nylon. Upon integration into garments, the sensor displays extremely high sensitivity with a resistance change of over 3000%, when worn on the elbow/knee during complete flexion-extension. The high sensitivity also enables the detection of minute finger motion during writing with a pen and minuscule movements due to muscle contractions.

The invention will now be further described with reference to the following Examples, which include experimental procedure and test results.

EXAMPLES

Example 1: Carbon Nanotube Coated Fabric-Based Thin and Flexible Pressure Sensors with Ultra-Wide Sensing Range This Example demonstrates a first aspect of the invention. Specifically, it demonstrates the fabrication and testing of a piezoresistive sensor made by an electrophoretic deposition process onto nonwoven aramid fibers. The resulting sensor was integrated into footwear and used to analyze and corroborate the forces involved in walking.

This example focuses on the development and validation of novel flexible piezoresistive sensors that can be integrated into functional fabrics and footwear. Formation of thin nanocomposite films of electrically conductive carbon nanotubes (CNTs) using a scalable electrophoretic deposition (EPD) technique enables the sensing functionality. Films in the range of 250-750 nm are created on a variety of natural (cotton, wool) and synthetic (aramid, spandex) fibers using the EPD process. In this embodiment, non-woven aramid fabric with randomly oriented fibers are coated with carbon nanotubes and polyethyleneimine (PEI). The aramid fabric is placed in direct contact with an electrode and PEI functionalized CNTs deposited under a DC electric field. The nanocomposite film first forms on the backing electrode and continues to grow around the aramid fibers and uniformly coats fibers throughout the thickness of the fabric.

The pressure sensor exhibits a large change in the in-plane electrical conductivity when out-of-plane pressure is applied. Formation of additional fiber-fiber contacts as well as the creation of sponge-like piezoresistive nanocomposite interphase between the fibers likely causes the in-plane electrical conductivity changes. The piezoresistive pressure sensors have an ultra-wide range of pressure sensing, from the tactile range (<10 kPa) to body weight range (~500 kPa) and very high pressures (40 MPa). This wide sensing range enables applications in broad fields such as e-skin for robotics, human-computer interaction, biomedical devices and gait analysis. The sensors are integrated into footwear and preliminary tests conducted to explore applications in gait analysis and validate the sensor response using a treadmill instrumented with force sensors.

1.1 Materials

An aqueous dispersion of 1 g/L of multi-walled carbon nanotubes (CM-95, Hanwha Nanotech) functionalized with PET (Sigma-Aldrich) is created using an ultrasonicated-ozonolysis method [18, 19]. The pH of the dispersion is reduced using glacial acetic acid (Sigma Aldrich, USA) to 6 in order to protonate the amine groups and form a stable dispersion of positively charged carbon nanotubes. The surface charge on the nanotubes enables them to be deposited using an electric field using a process known as electrophoretic deposition (EPD), shown FIG. 1 (upper left portion). FIG. 1 (upper right) shows a schematic diagram of a carbon nanotube functionalized with PEI.

A non-woven aramid fabric (20601, 50 g/m$^2$, Technical Fiber Products) of randomly oriented fibers (FIG. 1 (lower left)) was used as the carrier fabric for the deposition of the PEI-CNT nanocomposite film. The non-conductive aramid fabric was placed on a stainless steel electrode and was held in direct contact with the help of elastic bands. A stainless steel counter electrode was positioned at a fixed distance parallel to the electrode with the aramid fabric. The electrode setup with the fabric is immersed in the aqueous dispersion of carbon nanotubes and electrophoretic deposition was carried out using a direct current field strength of 22 V/cm. FIG. 1 (lower right) shows a scanning electron micrograph of an aramid fiber cross-sectioned using a focused ion beam (FIB), revealing a uniform coating of the PEI-CNT nanocomposite film. The dimensions of the specimen were 100×25 mm laminated between 0.12 mm thick plastic sheets using a heat laminating machine. To measure the electrical resistance, flash dry silver paint (04999-AS, Structure Probe, Inc., PA) was applied followed by attaching wires using conductive epoxy adhesive (40-3900, Epoxies etc, RI).

1.2 Mechanical Characterization

The pressure was applied to the fabric sensor using an electrically actuated load frame (Instron 8562) with a 100 kN load cell. The specimens were loaded to a pressure of 40 MPa followed by unloading. The electrical measurements for these experiments were performed using a Keithley 6430 sourcemeter. A constant voltage of 20V was applied while measuring the current to calculate the resistance. The load measurements were synchronized with electrical measurements using a customized LabVIEW interface.

1.3 Gait Analysis Tests on Treadmill with Force Sensors

To validate the sensor response for its application in gait analysis, sensors were integrated with footwear. Tests were conducted in the Neuromuscular Biomechanics Laboratory at the University of Delaware on an instrumented, split-belt treadmill (Bertec Corp., Worthington, Ohio). A single subject wearing the footwear integrated with the sensor walked at 0.75 m/s and 1.25 m/s for 1 minute. Treadmill force data was sampled at 2000 Hz and the sampling rate of the flexible pressure sensor was 30 Hz. The mass of the subject was 95 kilograms. Since the data acquisition system (DAQ) used in mechanical characterization was not portable, a smaller, easier to carry DAQ was built utilizing an Arduino Uno board powered by a 9V battery. A voltage dividing circuit is used for measurement of the resistance with a reference resistor of 10 kOhm. An additional 16-bit analog to digital converter is used to enhance the resolution of the measurement, and an SD card module stores the test data. The resistance change was normalized with respect to the baseline resistance of the sensor, i.e. when no load is applied.

In order to explore applications in detecting human motion, sensors were integrated into footwear and tests conducted on a treadmill instrumented with force sensors. The Aramid-CNT sensor was manufactured using the same processing conditions for the EPD process and attached in the hindfoot region of the footwear.

1.4 Results 1.4.1 Sensor Response to Transverse Compressive Loads

Figure 2A:
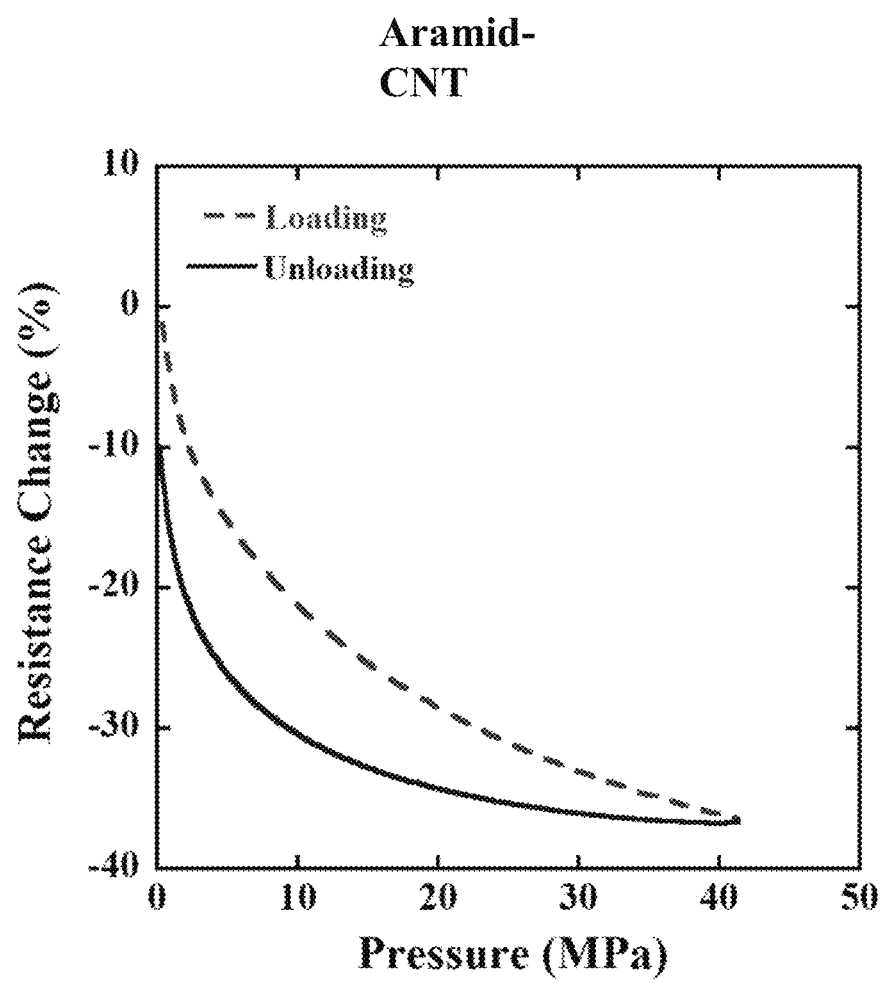
FIGS. 2B and 2C: Micrographs of the Aramid-CNT sensor after loading showing no significant damage.
FIG. 2D: Resistance response of the carbon fiber specimen.
FIGS. 2E and 2F: Micrographs of carbon fiber specimen showing extensive damage

The carbon nanotube coating on the aramid fibers imparts the sensing functionality to the fabric. An in-plane change in electrical resistance is observed on application of pressure because of the piezoresistive coating. FIG. 2A shows the change in resistance due to the applied pressure for the Aramid-CNT specimen. The change in resistance is likely because of the formation of additional fiber-fiber electrical contacts under applied pressure and the local piezoresistive response due to the compression of the carbon nanotube coating—where the fiber-fiber contact resistance changes due to the local deformation of the carbon nanotube coating.

Figure 2B:
Figure 2C:
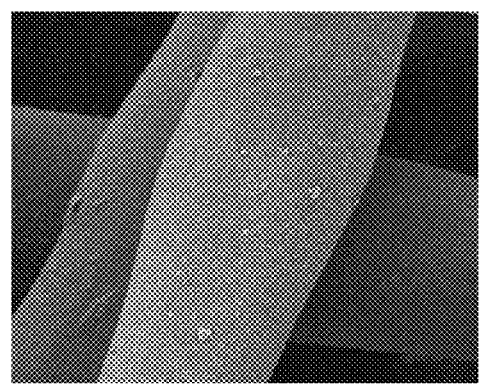

The slope of the resistance change at lower pressures is higher because the resistance change is dominated by the formation of fiber-fiber contacts. At higher pressures, the carbon nanotube coating is compressed on the surface of aramid fibers at the fiber-fiber contact points. Because of the piezoresistive nature of the carbon nanotube nanocomposite coating, the electrical resistance continues to decrease as the coating is compressed locally. FIG. 2B is a micrograph of the specimen after compression, showing no significant damage to the aramid fibers. FIG. 2C is an SEM micrograph showing localized deformation and flattening of the fibers at the fiber-fiber contact points. A slight decrease in the electrical resistance observed after the unloading of the sensors is possibly due to this local deformation of the fibers and increased fiber-fiber contact area.

Figure 2D:
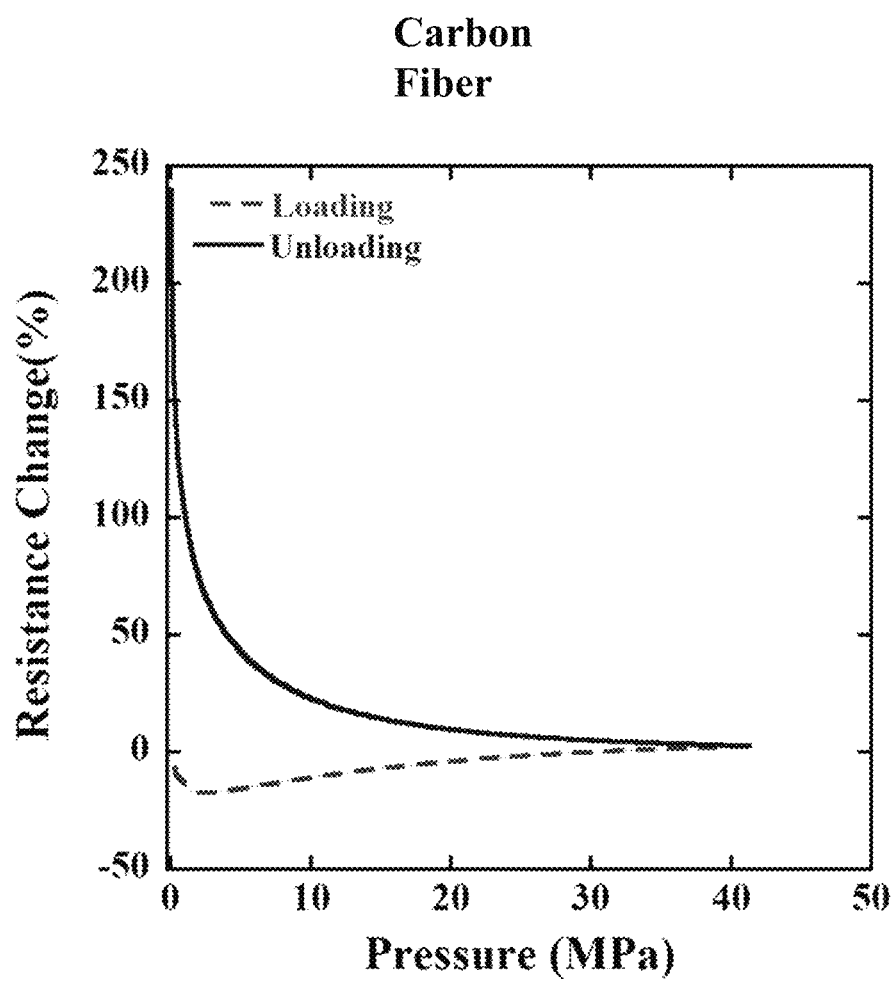
Figure 2E:
Figure 2F:
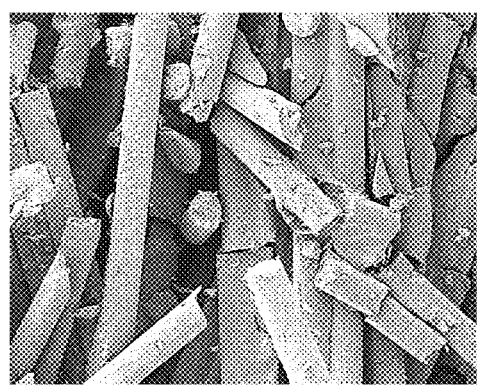

A similar non-woven fabric (20301, 50 g/m$^2$ Technical Fiber Products) of conductive carbon fibers was also subjected to the same pressure to further investigate the sensing mechanism. On application of pressure, the resistance decreases due to the formation of additional fiber-fiber contacts. However, unlike Aramid-CNT specimens, the electrical resistance of the loading curve shows a local minima at 2 MPa (FIG. 2D). Upon further loading the sensor resistance increases and plateaus near 0% resistance change at pressures above 30 MPa. During the unloading phase, the resistance continues to increases continuously and a permanent resistance change of almost 250% is observed when completely unloaded. FIGS. 2E and 2F show the damage to the carbon fiber specimen after loading. The carbon fibers fracture on the application of the compression load, likely due to the bending at the fiber-crossover points and the brittle nature of the fiber. For the Aramid-CNT specimen, no permanent change in resistance is observed when re-loaded below the initial peak load of 40 MPa. Loading for the first time likely results in the localized fiber flattening observed at contact points (FIG. 2C). After this initial localized deformation, the loading-unloading curves show a repeatable response.

1.4.2 Applications in Detecting Tactile Pressure and Human Gait Analysis

Figure 3:
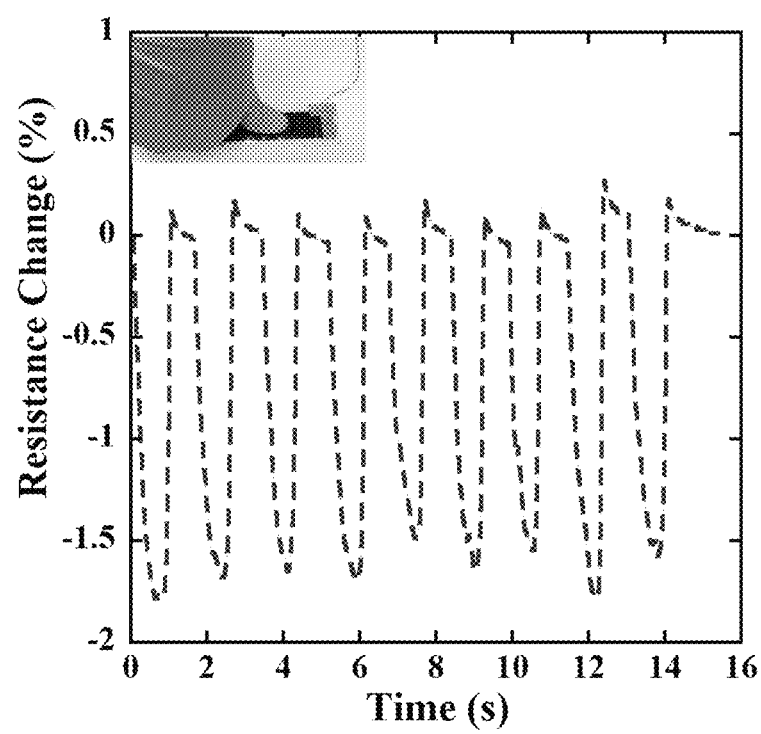
FIG. 3: Sensing response of Aramid-CNT sensor when subjected to pressures applied by a thumb

FIG. 3 shows the sensing response when pressure is applied using a thumb. A resistance change of about 1.75% is observed under tactile pressure. When the pressure is applied, there is an immediate decrease in resistance without any noticeable delay. Upon removal of pressure, the resistance returns to its original value and no permanent change in resistance is observed. There is a slight overshoot upon unloading likely due to the lifting of the laminated sheet off of the fabric sensor. The sensor recovers almost immediately after removing the force.

Figure 4:
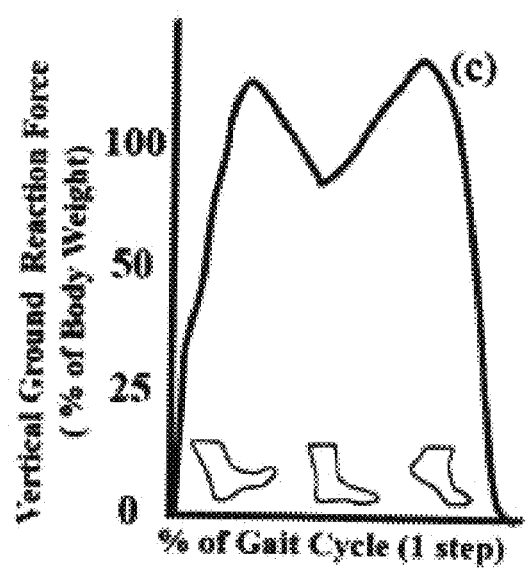
FIG. 4: Typical ground reaction force during a gait cycle

The sensor was placed in the hindfoot region of a sandal, and a human test subject walked wearing this sandal on an instrumented treadmill. FIG. 4 shows a typical vertical ground reaction force (GRF) during walking. The GRF is represented as a percentage of body weight vs. gait cycle. This force curve is sometimes called the 'M curve' due to its shape. At the instant just before the heel strikes, the force is zero between the foot and ground. As the heel contacts the ground, the GRF will increase rapidly as the weight is transferred from the opposite limb. The GRF soon reaches 100% of the body weight. Because the body center of mass is still moving downwards and decelerating, the GRF increases beyond the body weight. The GRF reduces slightly below the full body weight due to the change in acceleration and the shift of weight from the hindfoot to the forefoot. Eventually, the GRF decreases to zero as body weight is shifted to the other limb and the foot lifted off the ground.

Figure 5A:
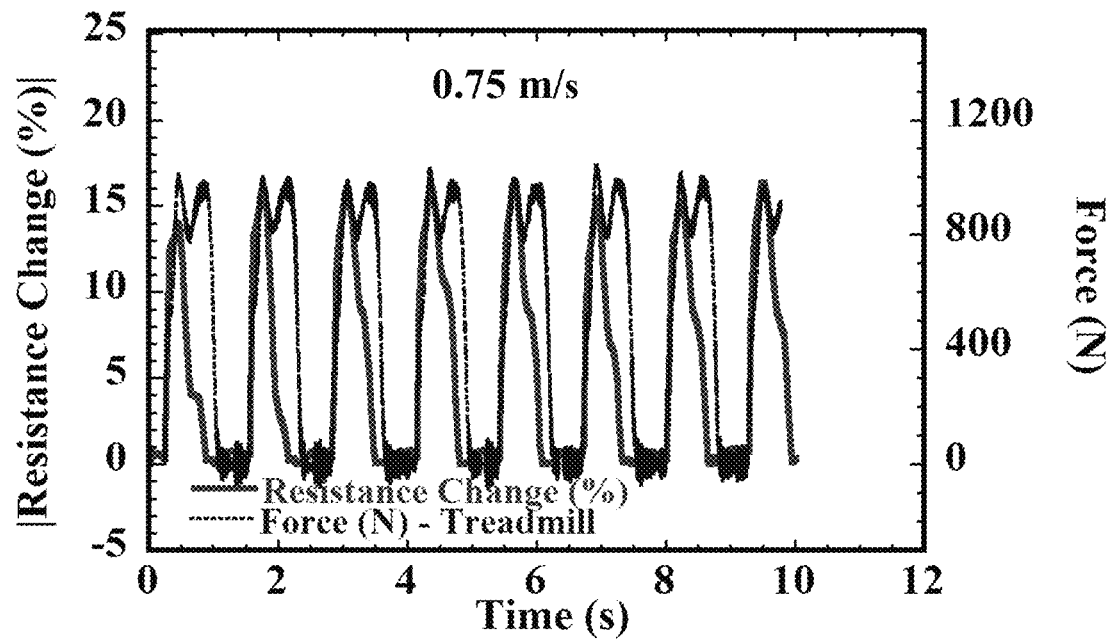
FIGS. 5A and 5B: Absolute magnitude of percentage resistance change measured using Aramid-CNT sensors and the force in Z direction measured using instrumented treadmill for (FIG. 5A) 0.75 m/s and (FIG. 5B) 1.25 m/s.
Figure 5B:
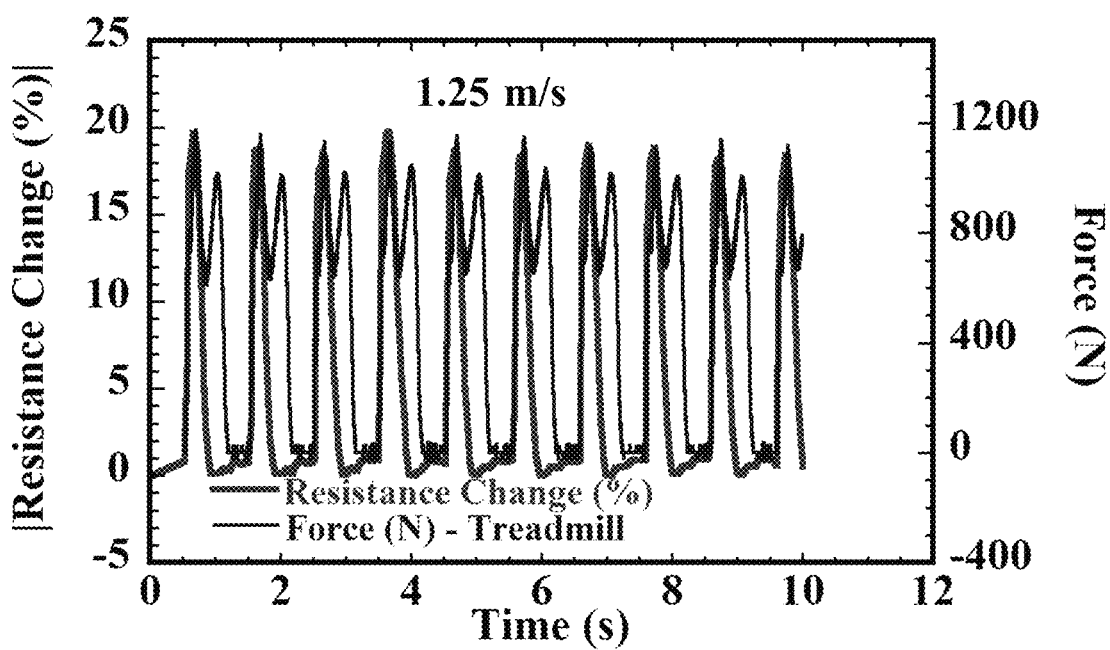
Figure 5C:
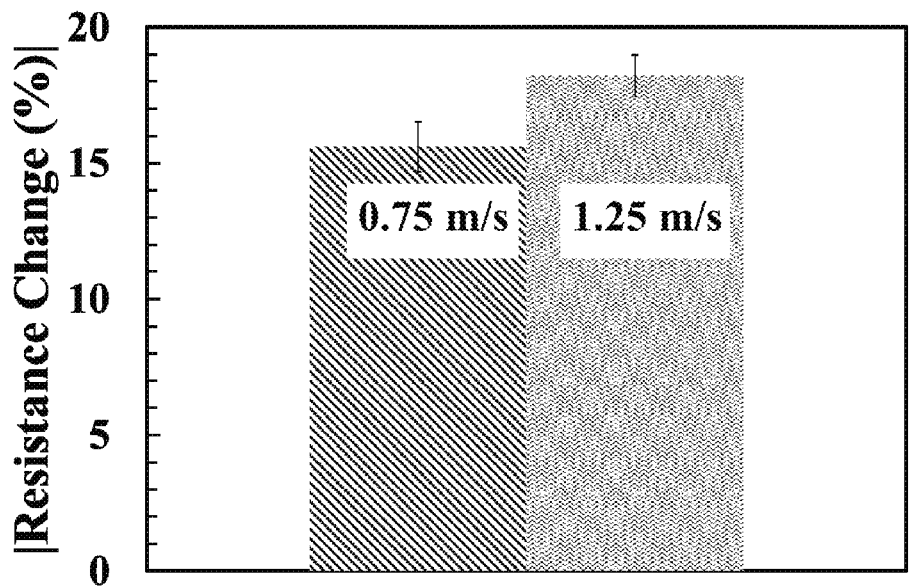
FIG. 5C: Average value of peak resistance change for different walking speeds

Walking at a faster speed generates a higher GRF. The average hindfoot peak GRF for each step is approximately 1000 N for 0.75 m/s and 1100 N for 1.25 m/s. FIGS. 5A and 5B shows the absolute magnitude of the percentage resistance change measured from the sensor and force in Z direction measured from the instrumented treadmill for tests conducted at 0.75 m/s and 1.25 m/s, respectively. Since the sensor was covering only the hindfoot region, only a part of the 'M curve' is captured by the resistance sensor whereas the force plate of the instrumented treadmill captures the entire 'M curve.' The shape of the resistance curve closely resembles the GRF measured using the force plates as seen in FIGS. 5A and 5B. The absolute magnitude of the percentage resistance change for 0.75 m/s is approximately 15% as compared to 18% for 1.25 m/s, shown in FIG. 5(c).

Figure 6:
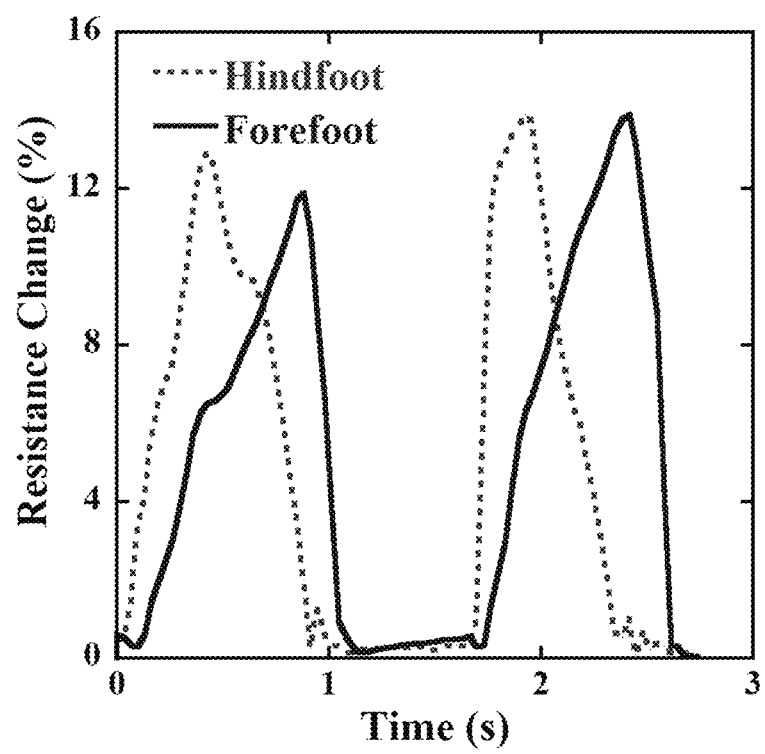
FIG. 6: Resistance change for a pair of sensors attached in the footwear. The sensing response is similar to a typical ground reaction force

To capture the entire 'M curve,' another sensor was attached in the forefoot. FIG. 6 shows the absolute magnitude of the percentage resistance change of both sensors for 2 steps. In a particular gait cycle, when the heel touches the ground, the pressure is applied on the hindfoot sensor which causes a resistance change. As the weight is being transferred to midfoot, the magnitude of resistance change of hindfoot sensor decreases and the forefoot starts to increase. Just before 'push off', when all the body weight is near the toe of the foot, the forefoot sensor reaches its peak value before decreasing to zero when the foot is off the ground. One of the reasons why the percentage resistance change curve is slightly different from the GRF curve is due to incomplete coverage of the sensors by the foot. Drift in the sensor signal, calibration of resistance to force and testing on more subjects are some of the challenges that need to be addressed going forward.

Example 2: Highly-Sensitive Carbon Nanotube Based Sensors Using Everyday Fabrics for Human Motion Analysis This Example demonstrates a second aspect of the present invention, namely, the fabrication and testing of highly sensitive, comfortable to wear sensors to measure a range of human joint motion. A dip-coating technique is developed to produce a thin nanocomposite coating on a commercially-available knitted fabric. The fabric sensor is then integrated into an elbow sleeve and the sensing response under elbow motion is examined.

Analyzing human motion is becoming increasingly important for patients requiring rehabilitation and athletes to improve performance. Motion capture cameras, currently used for human motion analysis are prohibitively expensive and complicated to use. There exists a critical need for developing innovative and cost-effective techniques to analyze motion outside of the laboratory. In this work, low-cost and comfortable wearable sensors can be created by coating everyday fabrics with nanocomposite coatings based on carbon nanotubes. A dip-coating process is used to coat fibers in a knitted fabric to create an elongation sensor. The nanocomposite coating makes the fabric electrically conductive and imparts piezoresistive sensing functionality where electrical resistance changes proportionally to mechanical deformation. A variety of mechanical tests are performed the electrical/mechanical coupling behavior. Preliminary results show ultra-high sensitivity with a resistance change of over 3,000% when an elbow sleeve sensor is worn while flexing. The sensors offer the possibility to be non-invasively integrated into clothing to create 'smart garments'.

2.1 Experimental

Sensors were prepared using a dip-coating process (FIG. 7A) where the fabric is coated using a sizing composed of an aqueous dispersion of multi-walled CNTs and polymers [8]. To lower the viscosity of the sizing, 1 part of sizing was mixed with 2 parts of ultrapure water by weight. To ensure a uniform dispersion of CNTs the diluted sizing was processed using a centrifugal mixer (THINKY® ARM-3 10) at 2000 rpm for 120 s followed by 30 minutes of sonication in an ultrasonic bath (Branson® 1510). A knitted fabric (nylon 44%, polyester 43%, and 13% spandex) commonly used in compression garments was chosen. The nylon and polyester provide excellent wear resistance, and spandex enables high stretchability and resilience. To coat the fabric the sizing was placed in a flat-bottomed container and a piece of fabric was dipped in the diluted sizing for 10 minutes on each side. The fabric was then dried in a convection oven for 60 mm at 150° C. Fabric before and after dip coating is shown in FIGS. 7B and 7C, respectively.

Figure 8:
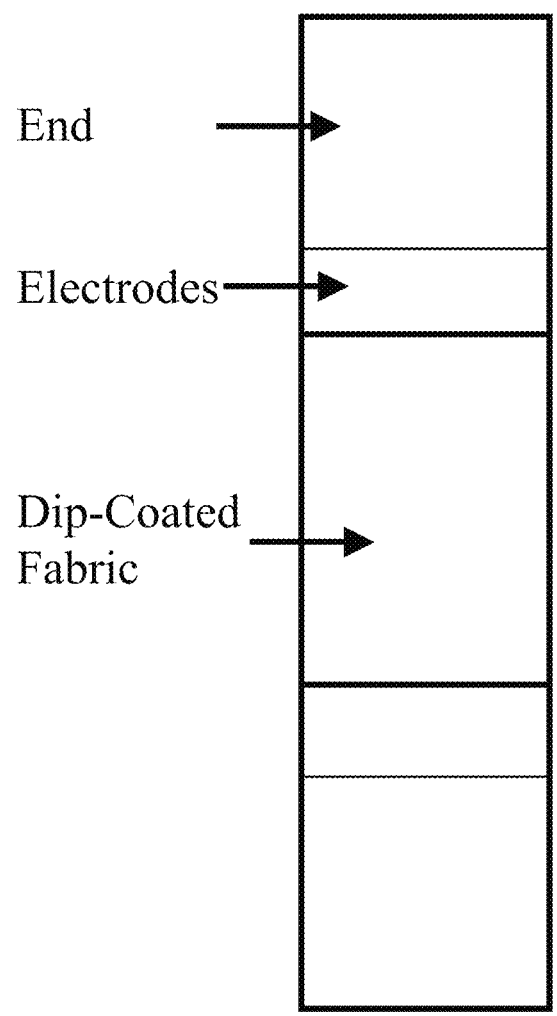
FIG. 8: Specimen for axial strain testing

Specimens for axial strain testing were cut to a size of 100×25.4 mm wide and electrodes and lead wires were attached to the specimen using conductive silver paint (Flash Dry, SPI Supplies, West Chester, Pa.) and a 2 part conductive silver epoxy resin (EPDXIES® 40-3900, Epoxies, Etc., Cranston, R.I.,). The electrodes were attached 60 mm apart as shown in FIG. 8. Non-conductive glass fiber end tabs were attached at the ends of the specimen to avoid shorting of the sensors in the steel grips of the testing machine. To test the sensor on the elbow, 130×38 mm strips of the coated fabric were stitched onto a compression sleeve made of fabric containing 82% nylon and 18% spandex and electrodes attached with a spacing of 101 mm.

Tensile tests were conducted under controlled-displacement using an electromechanical test machine (Instron Micron Tester 5848) with a displacement rate of 2 mm/sec. To test the response to joint motion; the sensor integrated into the arm sleeve is tested under varying degrees of elbow flex. Electrical measurements were made using a voltage-current meter (Keithley 6430 sub-femtoamp remote sourcemeter). The current was measured across the electrodes on the application of a constant source voltage, and resistance and extension measurements were synchronized using a customized LabVIEW program.

The morphology of the coating was examined using a scanning electron microscope (AURIGA 60 Crossbeam). To avoid sample charging, the specimens were coated with a thin (5 nm) conductive layer of Au/Pd using a vacuum sputter coater (Denton Desk IV, Denton Vacuum, LLC) for 60 sec. For the non-coated and CNT coated fabric, SEM was performed using an accelerating voltage of 1.5 kV and 3.0 kV, respectively.

2.2 Results and Discussion

Figure 9A:
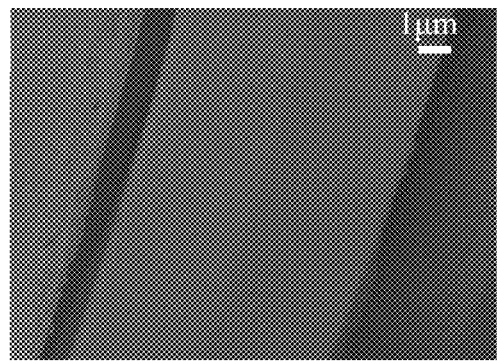
FIG. 9A: SEM micrograph of an individual fiber before coating.
Figure 9B:
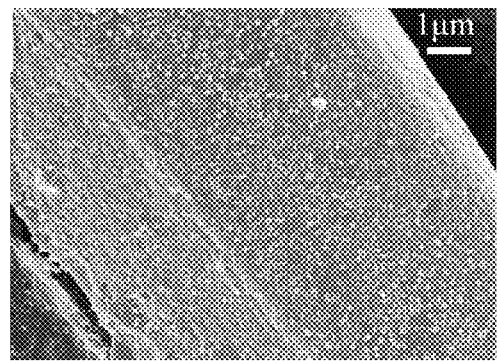
FIG. 9B: after coating with CNT sizing
Figure 10B:
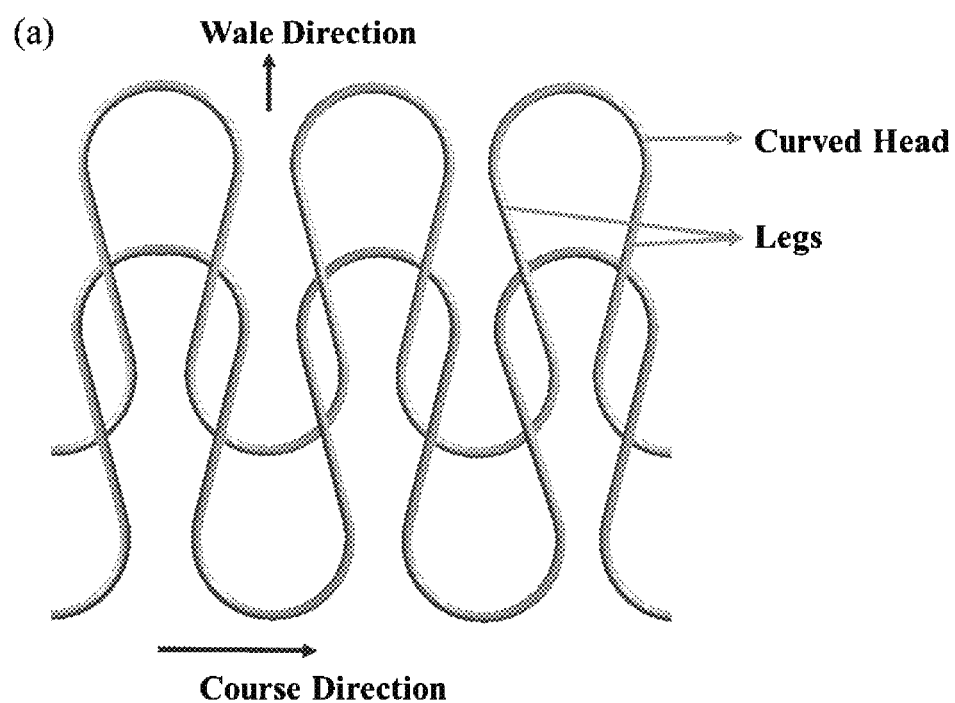
FIG. 10B: a schematic of the looped structure of a welt knitted fabric.
Figure 10A:
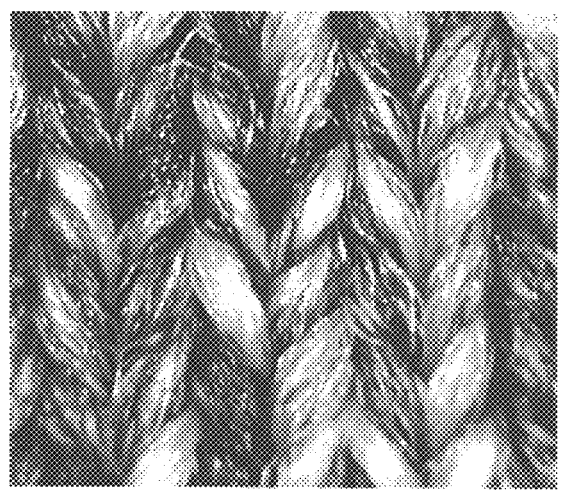
FIG. 10A: Optical micrograph of the knitted fabric.

FIG. 9A shows high magnification micrograph of a non-coated fiber. The surface of the fiber is smooth. FIG. 9B shows a fiber after dip coaling with CNT sizing. A uniform CNT nanocomposite coating is visible on the fiber surface. Optical microscopy of the fabric revealed that the knitted structure is a weft knit (FIG. 10A). FIG. 10B shows a schematic diagram of the looped structure of a weft knitted. The yarn in knitted fabrics makes symmetric loops above and below the mean path of the yarn. Loops are considered to have one head (curved part) and two legs (straight part), as shown. These loops are interlocked in course (weft) and wale direction and are easily stretchable in different directions, making knit fabrics flexible and drapable. [21]

Figure 11:
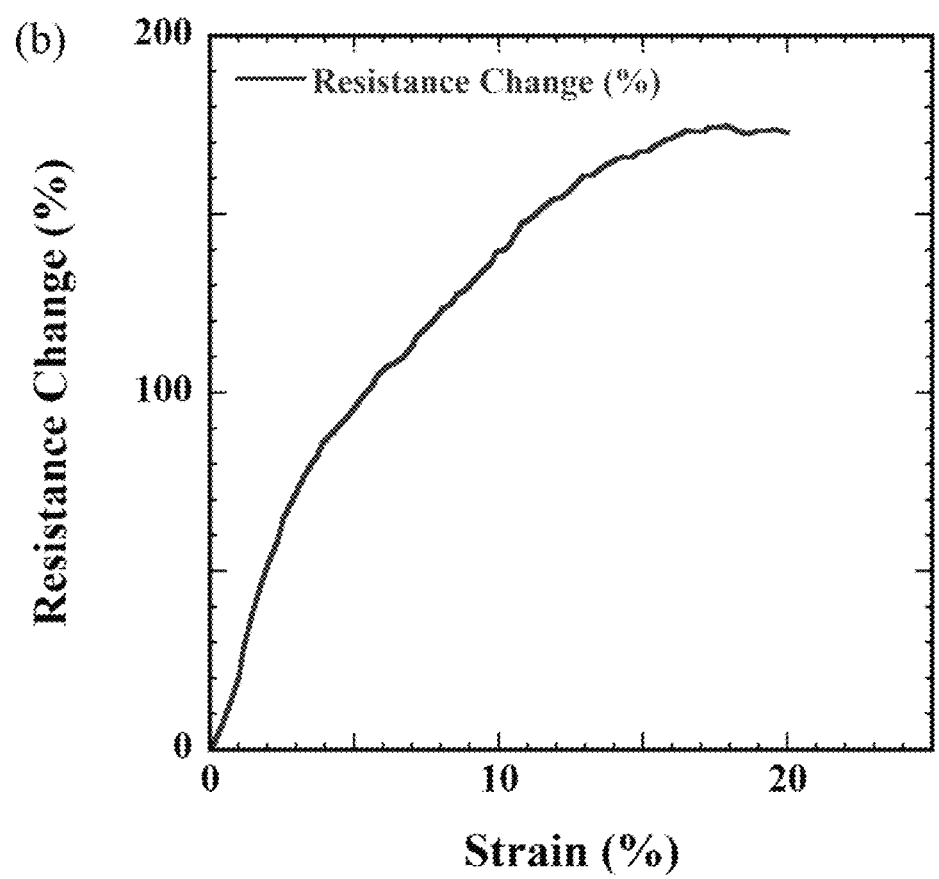
FIG. 11: Resistance-strain behavior of the CNT nanocomposite coated fabric

FIG. 11 shows the change in resistance versus strain of the fabric tested in the wale direction under tensile deformation, showing a resistance change of over 150% at 20% strain. When the knit fabric is stretched in the wale direction (in the direction of the loops), the leg height increases and the curved heads become narrower, which breaks down the connection points between adjacent loops in the same row. The piezoresistivity of a knit fabric coated with CNTs is likely due to both the piezoresistivity of the CNT composite coating as well as changes in the configuration of the conductive yarns. Nonlinearity of the response is possibly due to increasing contact pressure between the loops resulting in a decrease in yarn-yarn contact resistance along with decreasing resistance of the yarn bundle due to increased fiber-fiber contact under axial extension.

Figure 12:
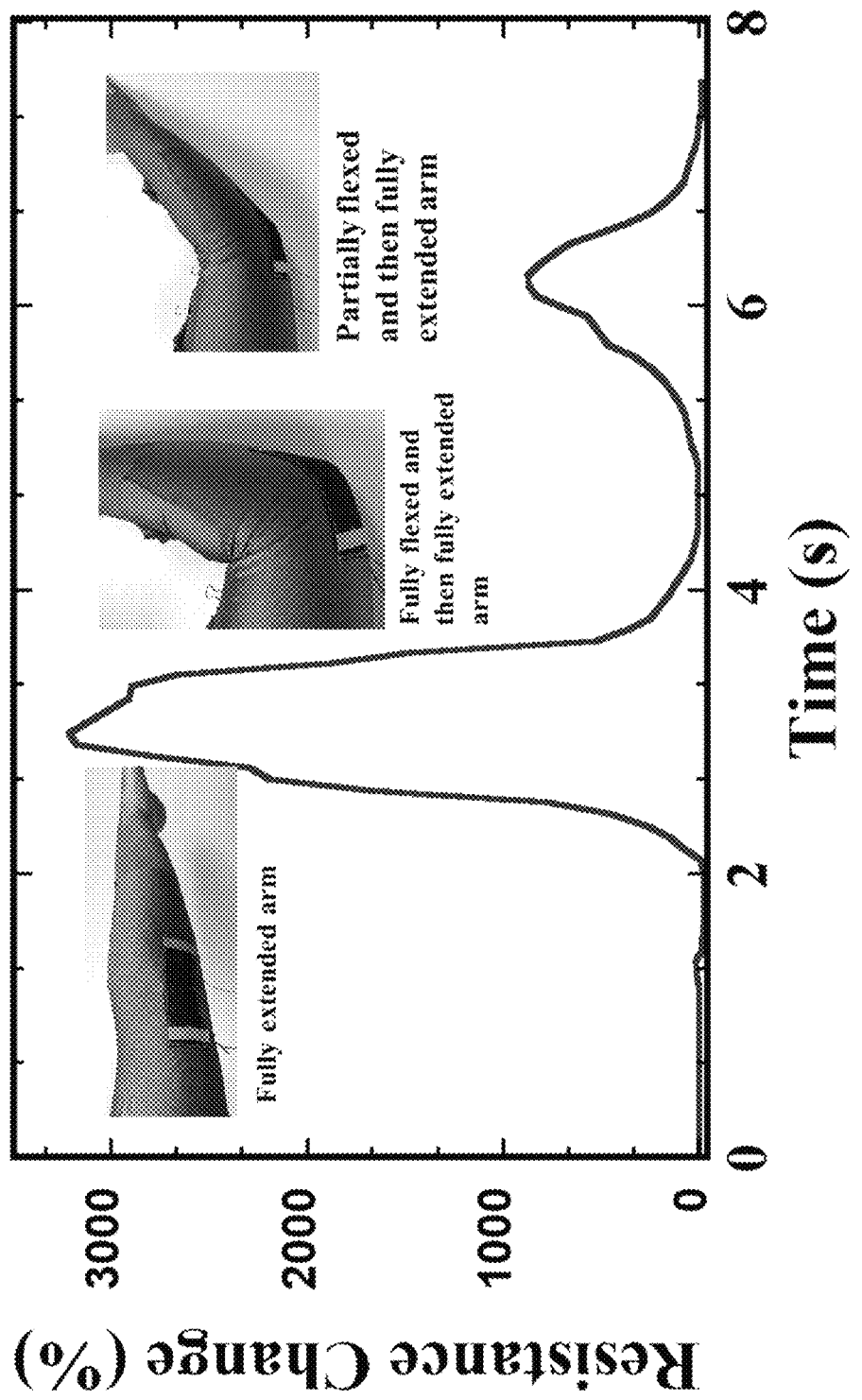
FIG. 12: Change in resistance in sensor on the elbow with fully and partially flexed arm

Alter coating, the stiffness and feel of the fabric is similar to the uncoated fabric making the sensor comfortable to wear. FIG. 12 shows the sensor response when sewn into a compression sleeve where the coated fabric is directly over the elbow joint. While maintaining a fully extended arm position, there is no significant resistance change. When moving the arm from fully extended to a fully flexed position (approximately 70°) a resistance change of more than 3,000% observed. For partial flex (approximately 30°), the resistance change is close to 1,000%. The resistance change in the garment is substantially higher than the resistance change due to simple axial stretching. The response of the sensor depends on the fabric deformation around the joint. It has been noted that the skin around the elbow joint extends 35 to 40 percent lengthwise and 15 to 22 percent circumferentially. [19] As a result, the sensor in the elbow sleeve is simultaneously subjected to axial and transverse extension.

Example 3: Carbon Nanotube Coated Textile Sensors with Ultrahigh Sensitivity for Human Motion Detection This Example demonstrates a third aspect of the instant invention. Specifically, we demonstrate a novel processing technique to create thin conductive films of carbon nanotubes on knitted fabrics to create flexible stretch sensors which are breathable, light-weight, and comfortable to wear. The sensing response is characterized using simultaneous mechanical and electrical characterization. Proof-of-concept is demonstrated by integrating the sensors in a knee sleeve and measuring the sensing response with knee flexion.

Highly sensitive stretch sensors are developed by coating knitted fabrics with carbon nanotubes. An innovative electrophoretic deposition approach is used to deposit a thin and conformal carbon nanotube coating on a nylon-polyester-spandex knitted fabric. The carbon nanotube coating is chemically bonded on the surface of the fibers and creates an electrically conductive network. As a result, these sensors display piezoresistivity; that is, the resistance of the sensor changes due to mechanical deformation. First, the sensing response under tension is characterized using mechanical testing equipment The sensors are then integrated into compression knee sleeves to investigate sensing response due to knee flexion. When the sensing fabric is stretched, an increase in electrical resistance is observed due to change in the microstructure of the knitted fabric and because of the piezoresistivity of the coating. Under knee flexion, a resistance change of over three thousand percent is detected. The carbon nanotube coated knitted fabrics as flexible stretch sensors have wide-ranging applications in human motion analysis.

3.1 Materials and Methods
3.1.1 Electrophoretic Deposition

Figure 13:
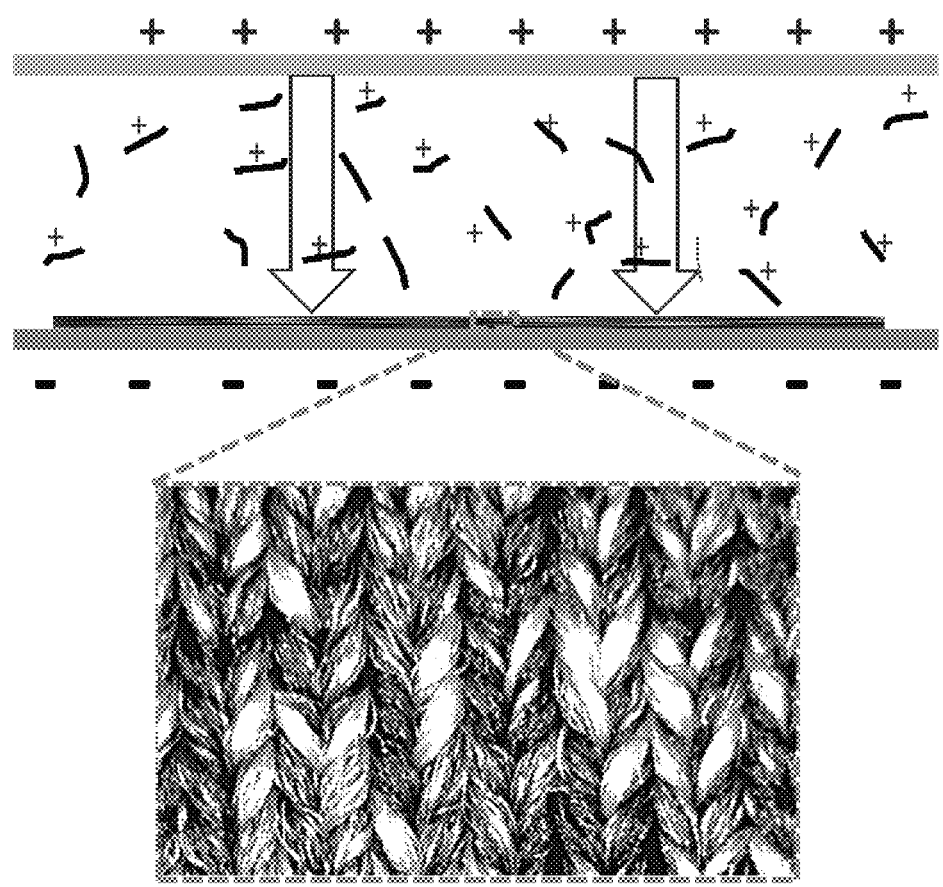
FIG. 13: (top) A schematic diagram of the electrophoretic deposition process with positively charged PU functionalized carbon nanotubes and (bottom) optical micrograph of the knit fabric showing the loop like microstructure.

Multi-walled carbon nanotubes (CM-95, Hanwha Nanotech) grown using chemical vapor deposition were dispersed in ultrapure water using an ultrasonication and ozonolysis approach as described by An et al. The concentration of the carbon nanotubes in the aqueous dispersion is 1 g/L. The dispersion is cooled to 5° C. in a water bath, and ozone gas is bubbled through the mixture at the rate of 500 mL/minute, which leads to the oxidation of the carbon nanotube surface. At the same time, the carbon nanotube-water mixture is sonicated using a 12.7 mm diameter horn sonicator (Sonicator 3000, Misonix). The sonicator is operated at 60 W with a 15 second on and 10 second off duty cycle. After a total sonication time of 16 hours, PEI (polyethyleneimine, $M_W$ 25,000, Sigma-Aldrich) is added to the dispersion followed by another 4 hours of sonication using the same duty cycle. Glacial acetic acid is then used to adjust the dispersion to a pH of 6 using glacial acetic acid (Sigma-Aldrich) to protonate the amine groups and form a stable dispersion of positively charged carbon nanotubes FIG. 13 shows the schematic diagram of the EPD process (top). The EPD process is enabled by the mobility of carbon nanotubes functionalized with PEI under mildly acidic conditions—developing a positive charge. The positively charged particles repel each other and create a stable dispersion. When an electric field is applied, the positively charged PEI functionalized carbon nanotubes deposit at the negative electrode. A non-conductive fabric placed in direct contact with the negative electrode allows a film of carbon nanotubes to deposit around the individual fibers.

3.1.2 Specimen Preparation and Testing

The knitted fabric used in this example consists of 44% nylon, 43% polyester, and 13% spandex. The dimensions of the specimen for tensile characterization was 100 mm×25 mm, and for a knee-sleeve was 130 mm×38 mm. The specimen was coated for 16 minutes using EPD under a field strength of 28 V/cm. Glass fiber/epoxy composite end tabs were attached to the specimen to hold it in the grips in the mechanical testing machine and to prevent electrical shorting. To accurately measure the electrical resistance of the sensor and minimize any contact resistance, conductive silver paint (Structure Probe. Inc.) and conductive epoxy adhesive (Epoxies, Etc.) were used to attach wires used as electrical leads. A mechanical testing machine (Instron 5848) was used to conduct the tensile tests, and a 2-wire method was used to measure the electrical resistance using a highly sensitive sourcemeter (Keithley 6430). The current was measured on the application of a constant voltage of 20 V. A customized LabVIEW program was used for measuring the electrical resistance and displacement of the testing machine crosshead simultaneously.

3.2 Results

Figure 15:
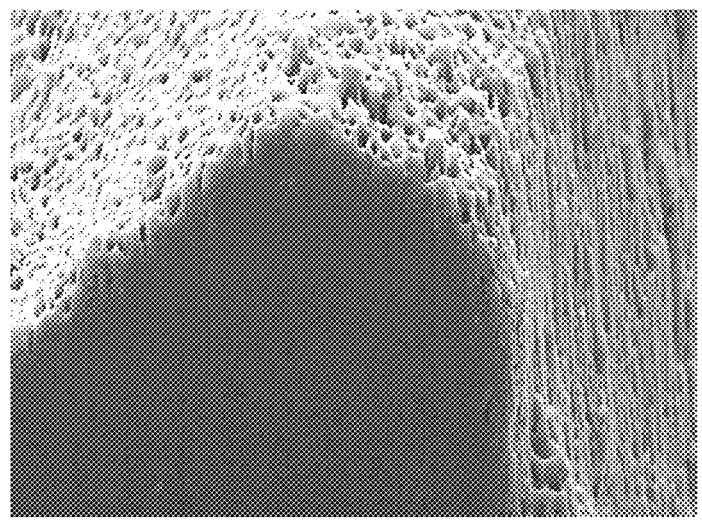
FIG. 15: A scanning electron micrograph of a fiber cross-sectioned using focused ion beam showing uniform coating of carbon nanotubes

The morphology of the carbon nanotube coating on the knitted textiles was characterized using scanning electron microscopy. FIGS. 14A and 14B are images of the fabric before and after coating with carbon nanotubes. FIGS. 14C and 14D show scanning electron micrographs of a non-coated and coated fabric, respectively. The surface of the non-coated fibers is smooth, whereas, for the coated fibers, a uniform film of the PEI functionalized carbon nanotubes is visible on the surface of the fibers. FIG. 15 shows a cross-sectioned fiber using a focused ion beam (FIB). A uniform porous nanocomposite film of PEI functionalized carbon nanotubes can be observed.

Figure 16:
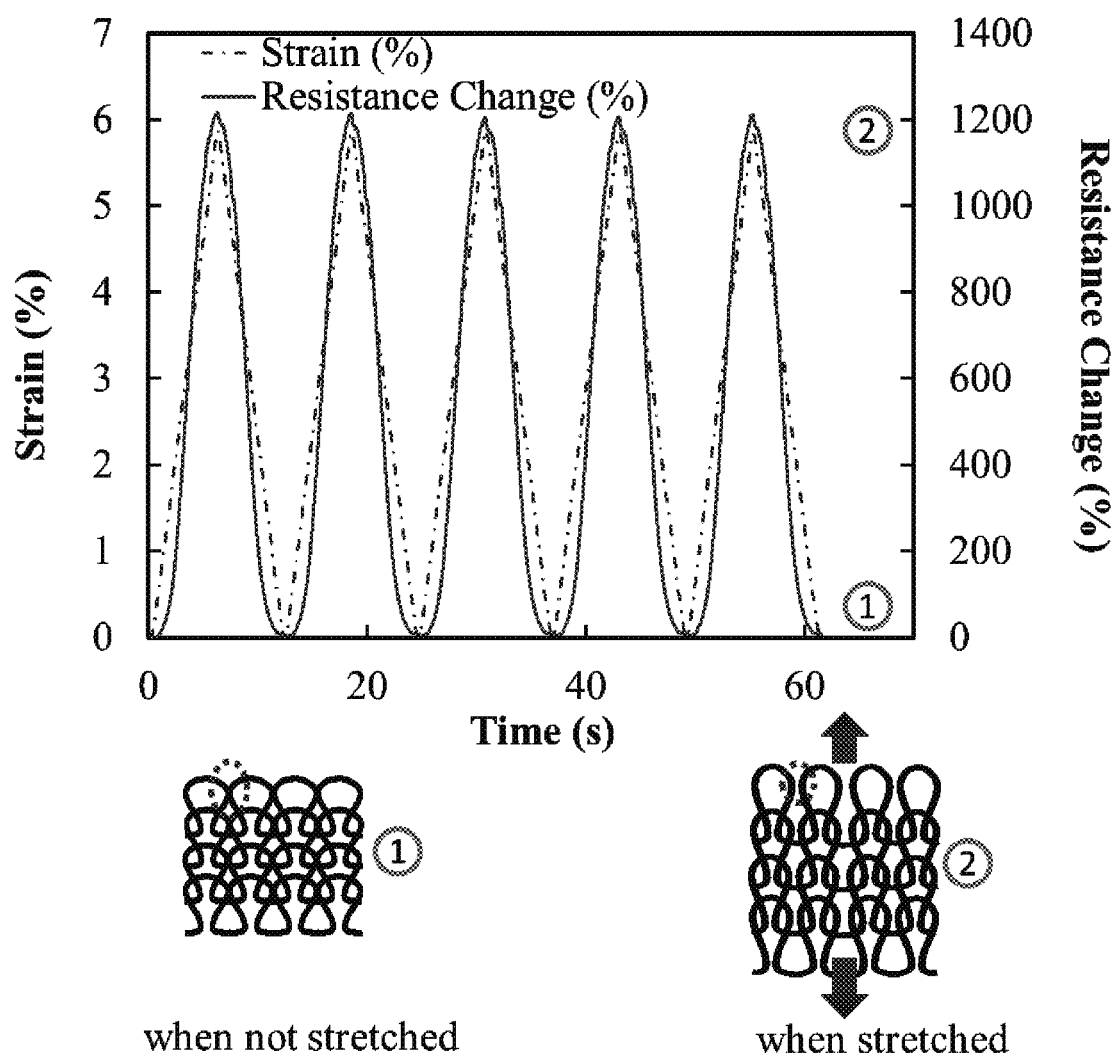
FIG. 16: Strain and resistance change (%) response of a sensor tested for 5 cycles in tension to a strain of 6%. A schematic showing the looped structure of knitted fabric (1) when not stretched and (2) when stretched

FIG. 16 shows the strain and percentage resistance change for tension tests. The specimen was tested for 5 cycles to a strain of 6% and a maximum resistance change of about 1200% was observed. The high stretch-ability and drapability of the knitted fabrics are due to the looped structured of the fabric. When stretched, the height of the loop increases and the loops become narrower because of which, the connection points between the adjacent loops in the same row are broken. This leads to a change in bulk electrical resistance. The piezoresistive response of the carbon nanotube coated knitted fabric is likely due to two key mechanisms: (1) breakage of contact points between the adjacent loops and (2) piezoresistivity of the carbon nanotube coating.

Figure 17A:
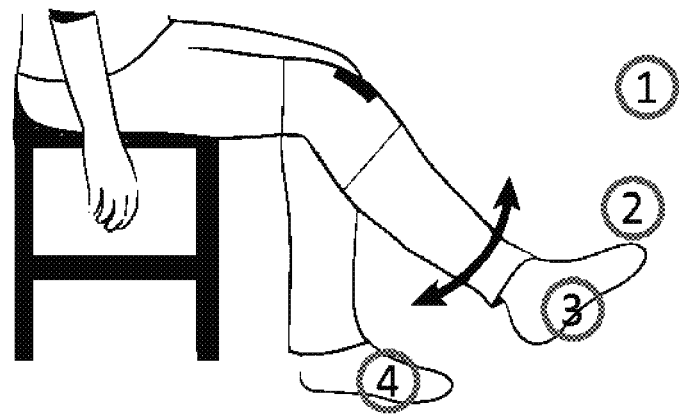
FIG. 17A: a schematic of the test showing the 4 positions to which the knee was flexed.
Figure 17B:
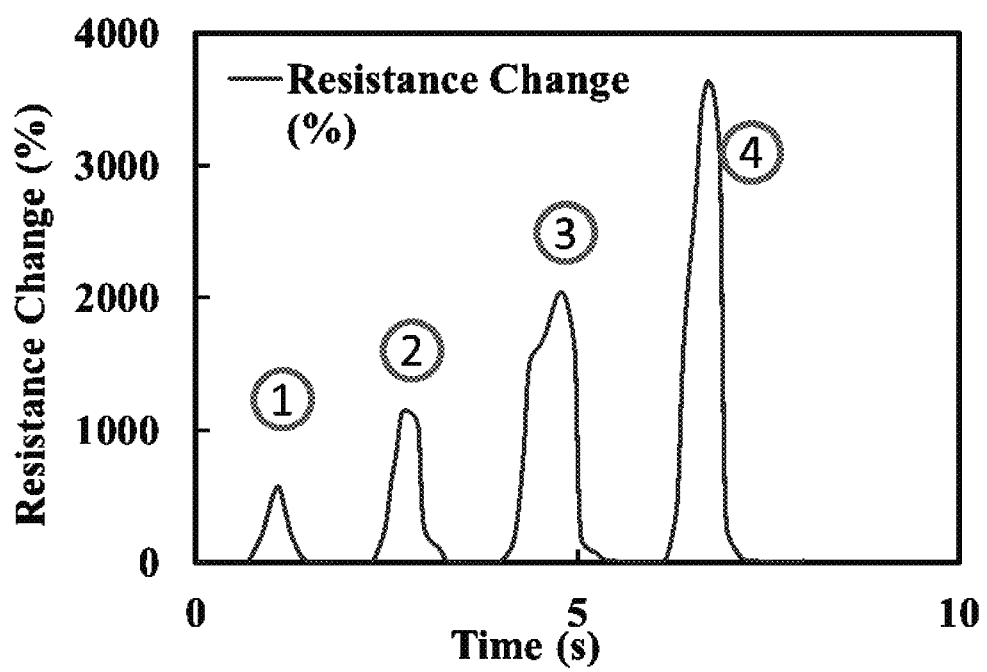
FIG. 17B: resistance response of the sensor integrated into knee-sleeve under increasing flexion

A human test subject donned the sensor-integrated knee sleeve with the sleeve positioned at the knee joint. The sleeve is also made using a stretchable knitted fabric with 82% nylon and 18% spandex. The sensor is integrated by sewing using a zig-zag pattern to allow for stretch-ability. Because the carbon nanotube coating is thin, lightweight, and conformal, the stiffness and texture of the fabric are quite similar to the non-coated fabric, making it comfortable to wear. FIG. 17A shows the schematic of the test conducted with a subject sitting on the chair, with increasing knee flexion in each movement. FIG. 17B shows the resistance response of the sensor for the test. With each motion as the leg is bent through a large angle, the resistance change increases. At a flexion of around 100 degrees, a resistance change of over 3,000% is observed. Even at partial flexion, a significant resistance change is measured. The resistance change for the knee-sleeve is significantly higher than the conventional tensile tests. This is likely due to the deformation of the sensors along the length as well as circumferentially, which is not the case for simple tensile tests. The sensor in a knee sleeve is subjected to both axial and transverse stretching simultaneously.

Example 4: Carbon Nanocomposite Sensor Having Very High Sensitivity

This Example demonstrates a fourth aspect of the invention, namely, that the piezoresistive sensors of the present invention can be extremely sensitive and can pick up and detect highly precise, refined, delicate low-pressure movements such as the motions of the fingers involved in an activity such as printing/handwriting. Proof-of-concept is demonstrated by configuring the sensor as a finger sleeve.

In this example, a comfortable to wear, flexible wearable sensor with ultra-high sensitivity using commercially available fabrics is demonstrated. An efficient electrophoretic deposition technique (discussed above) is used to create a conductive nanostructured composite coating on fabrics such as polyester, rayon, wool and nylon. Carbon nanotubes are functionalized with a dendritic polyethyleneimine (PEI) to create an aqueous dispersion and deposited using a direct current (DC) electric field. A very thin (~1 μm) film of PEI functionalized carbon nanotubes is created on the surface of the fibers. Due to the thin and porous nature of the coating, there is no significant change in the texture and the feel of the fabric, and the porosity is also maintained, making it comfortable to wear. The carbon nanotube coating is robustly bonded to the fibers and does not deteriorate when subjected to sonication and tape tests. Upon integration into garments, the sensor displays extremely high sensitivity with a resistance change of over 3000%, when worn on the elbow/knee during complete flexion-extension. The high sensitivity also enables the detection of minute finger motion during writing with a pen and minuscule movements due to muscle contractions.

4.1 Specimen Fabrication, Experimental Details and Electron Microscopy

An aqueous dispersion of multi-walled carbon nanotubes functionalized with polyethyleneimine (PEI) with a concentration of 1 g/L is prepared using the approach discussed in Example 1. The non-conductive fabrics to be coated are backed against stainless steel (316) electrode, which is connected to the negative terminal because the carbon nanotubes are positively charged. Elastic bands are used for ensuring slight tension in the fabrics to maintain uniform contact with the electrode. A counter electrode also fabricated using stainless steel is placed parallel to the anode at a fixed distance using insulating spacers. The assembly is immersed in a glass container with the carbon nanotube dispersion following which electrophoretic deposition is conducted using a Direct Current voltage. Following the coating, the fabrics are dried in an oven at 120° C.

The fabric used for electromechanical characterization is a commercially available weft knitted fabric consisting of 44% nylon, 43% polyester and 13% spandex. After the coating, flash dry silver paint and two-part conductive epoxy is used for painting the electrodes and attaching the lead wires to reduce the contact resistance and measure the electrical resistance accurately. The mechanical tests were conducted using a screw-driven load frame Instron 5567 under a displacement-controlled setting.

Scanning electron microscopy images were captured using an Auriga 60 Crossbeam electron microscope with an accelerating voltage of 3 kV for the carbon nanotube coated specimens. The specimens were coated with a Pd/Au layer using a sputter coater to reduce the charging of the specimen. The cross-section of the fiber is cut using a focused ion beam (FIB). First, a rough cut is made, which is followed by a finer cut with a FIB probe setting of 30 kV and 240 pA.

Figure 18:
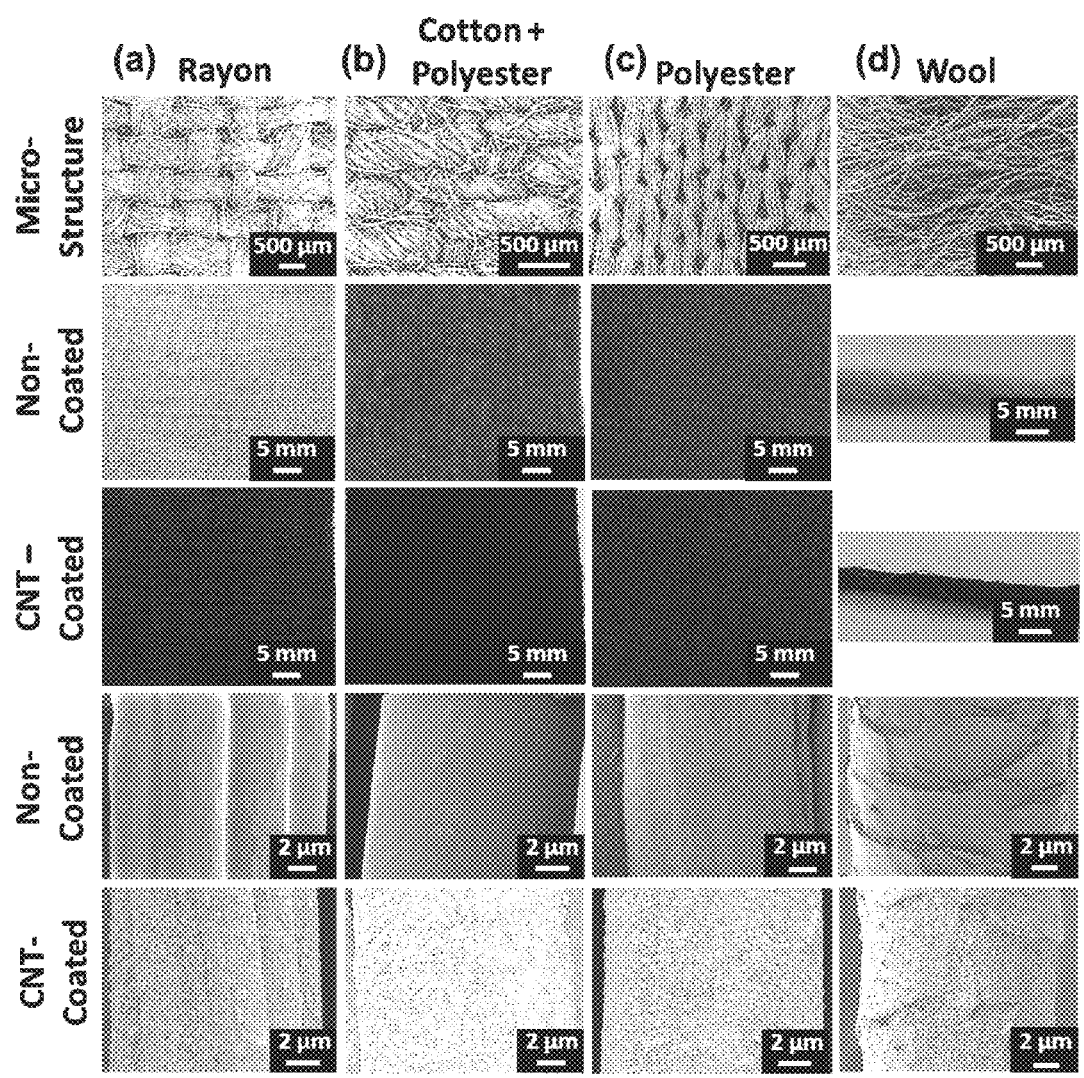
FIG. 18: Carbon nanotubes deposited on various types of fabrics with different weave patterns and knit structures. The individual fibers also have a distinct microstructure. A uniform coating of carbon nanotubes is deposited on all the fibers within the bundles for materials such as rayon; denim, a mixture of cotton and polyester with elastane; knitted polyester fabric; and twisted wool yarn

4.2 Deposition of Carbon Nanotubes on Different Materials with Varying Microstructures A critical advantage of the EPD process is the ability to coat a variety of natural and synthetic fibers such as rayon, cotton, polyester, nylon and wool, as shown in FIG. 18. Fibers having a very distinct microstructure as well as fabrics with various types of microstructures and weaving patterns are coated with carbon nanotubes. The first column of FIG. 18 shows rayon fabric with a plain weave coated with carbon nanotubes. The scanning electron microscope (SEM) image shows very distinctive features such as linear striations along the length of rayon fiber. Despite the structure with intricate features, all the fibers within the fabric are uniformly coated.

The second column shows images of a Denim material consisting of cotton, polyester and elastane. The third column features pictures and micrographs of knitted polyester fabric, and the fourth column displays a twisted wool yarn with and without carbon nanotube coating. The microstructure of the wool shows a rough, irregular surface with a scale-like structure. Using the same setup, carbon nanotubes were deposited on different fabrics having a varying material composition, weaving patterns, and microstructures.

4.3 Piezoresistive Knit Fabrics Coated with Carbon Nanotubes

Figure 19C:
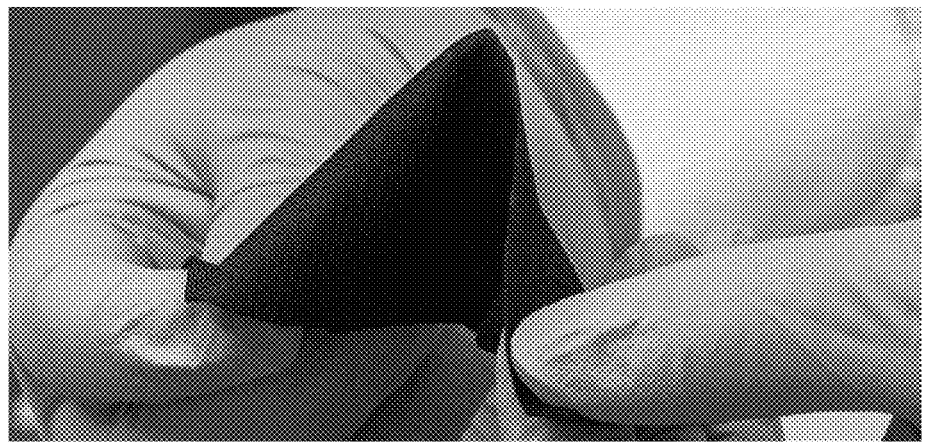
Figure 19D:
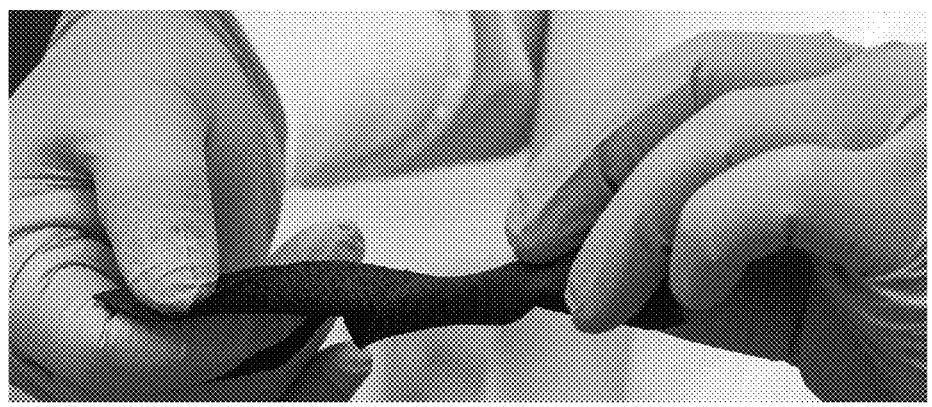
Figure 19E:
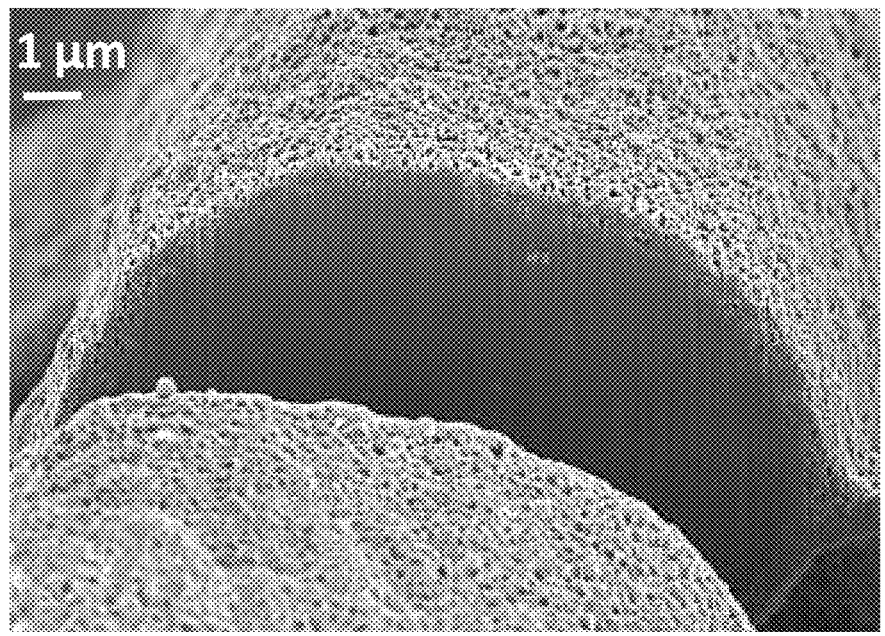

For wearable sensors, flexibility, lightweight, and comfort being the essential parameters, a commercially available knit fabric consisting of polyester, nylon, and spandex was selected for electromechanical characterization and prototype testing on the elbow, knee and fingers. FIG. 19A shows the fabric without coating at different length scales. The SEM micrographs show that the surface of the fibers is relatively smooth with a few minute features. FIG. 19B is after the fabric is coated with carbon nanotubes using EPD. The color of the fabric has changed to black, and the SEM images show a uniform thickness coating of functionalized carbon nanotubes on all the fibers throughout the fabric thickness. As the coating is thin, there is no significant change in the stiffness and texture of the fabric that can be felt by the end-user. FIGS. 19C and 19D show the stretchability and the flexibility of the carbon nanotube coated fabric. Due to the conformability of the nanocomposite coating, the coated fabric is still flexible and can be easily integrated into garments using existing tools and setup used in the industry. FIG. 19E is a cross-section of fiber from the coated fabric cut using a focused ion beam. A porous nanocomposite coating with uniform thickness all around the fiber can be observed. The thickness of this nanocomposite coating can be controlled by varying the EPD process parameters such as voltage field strength and time of deposition.

4.4 Robustness and Durability of the Carbon Nanotube Coating

Figure 20A:
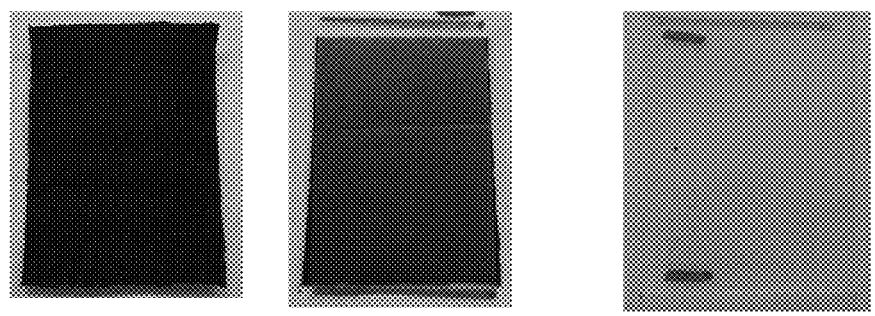
FIG. 20A: Tape tests using a Scotch™ tape showing the robust nature of the coating with no significant weight loss after the test or loss of coating. Sonication of the coated fabric for 15 minutes in (FIG. 20B) tap water and (FIG. 20C) tap water with detergent. The micrographs show that the coating is not deteriorated after sonication in either case.
Figure 20B:
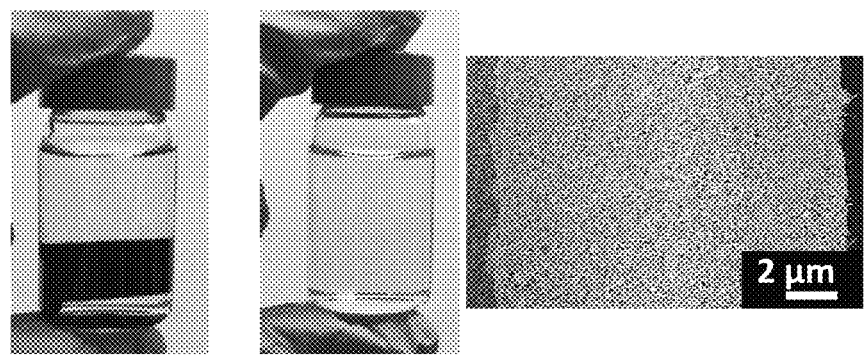
Figure 20C:
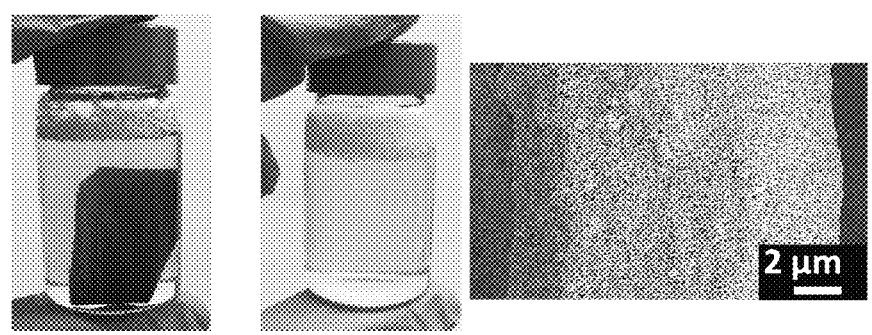

To check the robustness of the bonding of the carbon nanotube coating on the surface of the fibers, tape tests and sonication tests were conducted. FIG. 20A shows the tape test where a Scotch™ tape (3M) is applied to the coated fabric, followed by applying pressure by hand and then keeping a 500 g block for 3 minutes on tape and subsequently pulling off. After pulling off the tape, a few small fibers and some black residue was observed along the edge of the specimen, which is likely because of the loose fibers present due to cutting of the coated fabric with the scissors. When the fabric was weighed before, and after the tests, there was no reduction in weight when measured using a scale with a weight measuring capability of 0.0001 grains. For the sonication tests, the fabric was placed in a glass vial containing tap water (FIG. 20B) and tap water with detergent (FIG. 20C) and sonicated in a bath sonicator for 15 minutes. Like the tape tests, there was no significant reduction in weight. Observing with naked eyes, there was no residue of the carbon nanotubes in the water after the tests indicating a robust bonding of the coating to the fabric.

4.5 Characterizing the Sensing Response Using Mechanical Testing Machines

Figure 21:
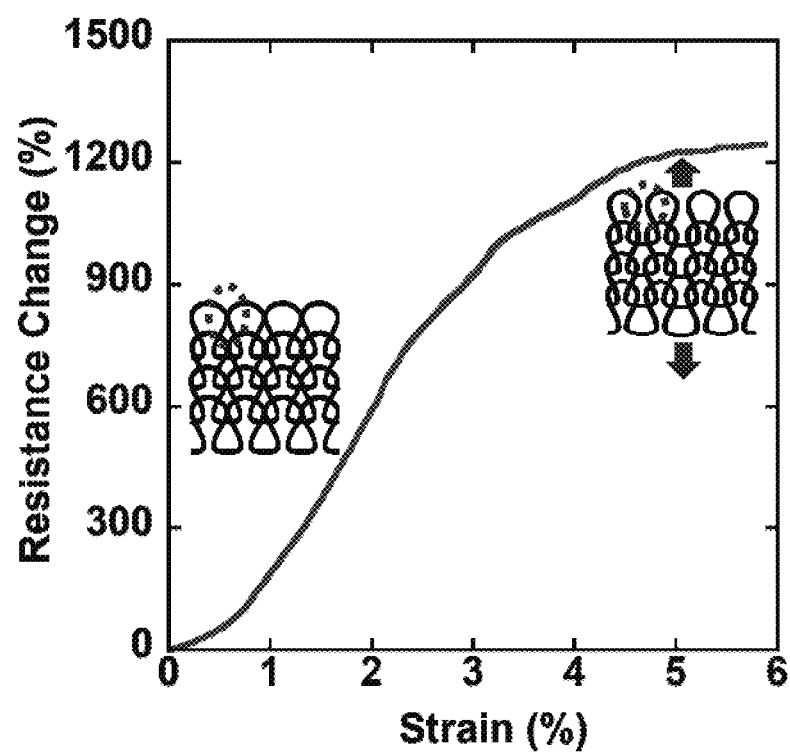
FIG. 21: Resistance response for a specimen tested under tensile deformation displaying a very high sensitivity. The resistance change is due to multiple effects such as an increase of tunneling gap between nanotubes when the fibers are stretched and due to the change in the shape of the loops in knit fabrics due to extension.

FIG. 21 shows the electromechanical characterization response when the sensor is tested in tension along the wale direction (in the direction of the loops). Different mechanisms at varying length scales play a critical role in the change in resistance of the sensing fabric (i) at the fabric level, the changing shape of the knitted loops, (ii) at the yarn or the fiber bundle scale, the fibers coining closer to each other due to applied tension and (iii) at the fiber scale, the tunneling and the number of contact points between the carbon nanotubes in the coating.

Due to the elastic nature of the fibers and the presence of loops in the microstructure, at lower strains, the slope of the resistance change is less. After the initial stretching at a strain of about 0.8%, the slope of the resistance change curve increases. The resistance increase is likely because of the increase in tunneling gaps between the carbon nanotubes in the coating as the fibers are stretched and the change in the shape of the looped structure. Upon stretching, the curved part or head of the loop becomes narrower, and the length of the leg of the loop becomes longer, making the columns of the loop narrower and longer. As a result, the loops break contact with the loops in the adjacent columns creating a large change in the electrical resistance. After a strain of about 6%, the slope of resistance change decreases. This is possibly due to multiple mechanisms, the transverse contraction due to Poisson's effect at the fabric scale, increasing contact points between the fibers in a yarn, and increasing contact pressure at crossover points of the loops in the same column.

Figure 22:
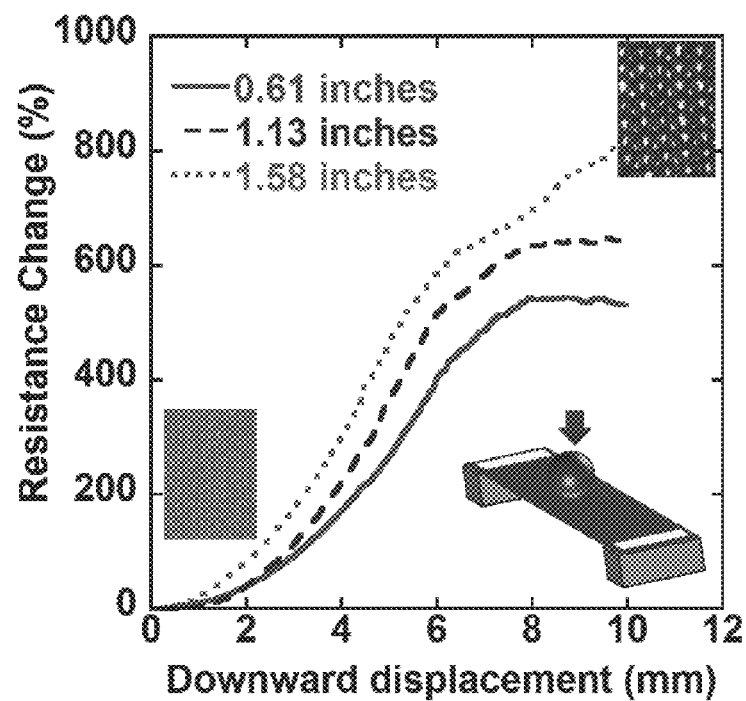
FIG. 22: Resistance response when spheres of different diameters are pushed into the fabric, causing biaxial stretching locally. The fabric is supported at two ends, and the sphere makes contact at the center of the fabric.

FIG. 22 shows the sensing response when spheres made of non-conductive material of varying diameters are used to push onto a fabric supported at two ends. Due to the spherical shape, at the point of contact, the fabric is stretched biaxially, along the length and the width. Larger the diameter, higher is the resistance change. The increase in resistance is due to the decrease in contact points between the yarns forming the loop and the increase in tunneling gaps between the carbon nanotubes when the fibers are stretched. After the displacement of about 6 mm, the resistance curve plateaus due to increasing contact points between the fibers in the yarn, increasing contact pressure at the crossover points of the loop, and due to the pressure of the sphere on the fabric.

4.6 Applications of Wearable Sensors in Human Joint Motion Detection

Other than user comfort, an important point to consider for wearable sensors is the ease of integration in clothing and garments. Since the fabric coated with nanotubes is very similar to the non-coated fabric (which is used for making garments), it can be sewed into clothing using readily available tools and manufacturing setup. In this study, the sensing fabric is integrated into garments with a sewing machine using a zig-zag sewing pattern for stretchability.

4.7 Range of Motion at Elbow

The sensing response when the sensor is integrated into a compression fit sleeve was similar to that shown in FIG. 12 in Example 2. The sleeve does not slide over the arm due to the flexing movements. When the arm is held straight, the sleeve is not stretched, and hence there is no change in resistance. Upon flexing the arm, the sleeve is stretched in both directions along the length of the arm and perpendicular to it. This causes a huge change in resistance, which is proportional to the amount of flexing of the arm. Here, in the present example, at a partial flex of ~30 degrees, a resistance change of 1250%, and at midflexion (~90 degrees), a remarkable 2750% resistance change is observed. The change in resistance is significantly higher for these tests as compared to the mechanical characterization in FIG. 21 likely because of the biaxial stretching and the constraint due to the compression fitting of the sleeve that minimizes the Poisson's contraction and lateral fiber movements.

Figure 23:
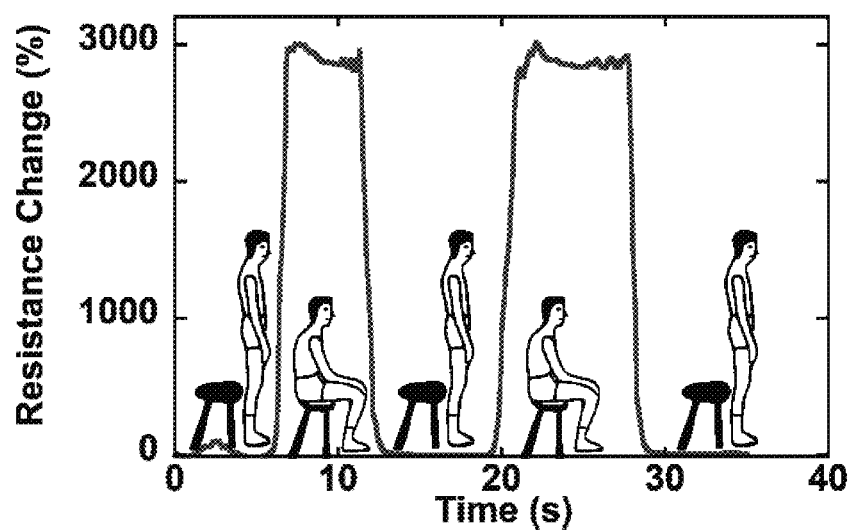
FIG. 23: Resistance change when the sensor is integrated into a compression knee sleeve, and the subject moves from standing to sitting position and back. As the knee is bent, it causes biaxial stretching of the sensor triggering an increase in the electrical resistance.

In FIG. 23, the sensor is integrated to into a similar sleeve worn over the knee. At ~3 seconds, even when a slight jerk like motion is given at the knee by the subject, an increase in resistance is observed. When the subject sits on a chair, the knee is bent, causing a tremendous increase in resistance of ~3000%. As the subject continues to sit, the resistance remains constant until the subject stands back up, and the resistance returns to the original value and stays constant until the next motion.

Figure 24A:
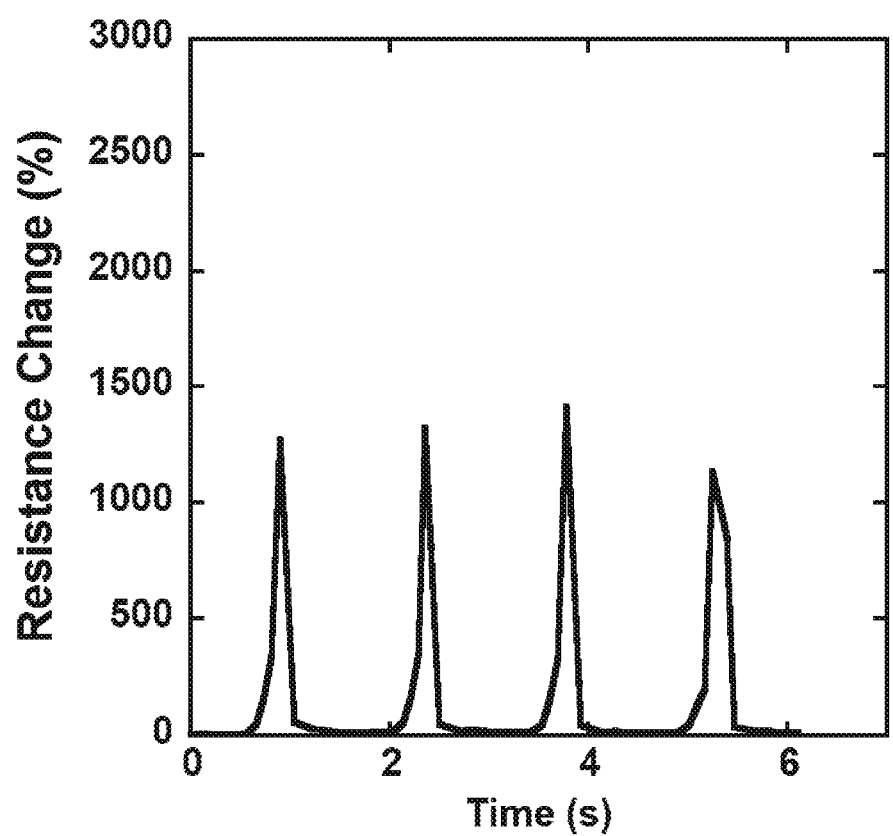
FIGS. 24A and 24B: Sensing response when the sensor is integrated into a compression knee sleeve, and the subject is walking on (FIG. 24A) flat ground and (FIG. 24B) up the stairs. The resistance change is significantly more when walking up the stairs as compared to walking on the flat ground because the knee is bent more when walking up the stairs.
Figure 24B:
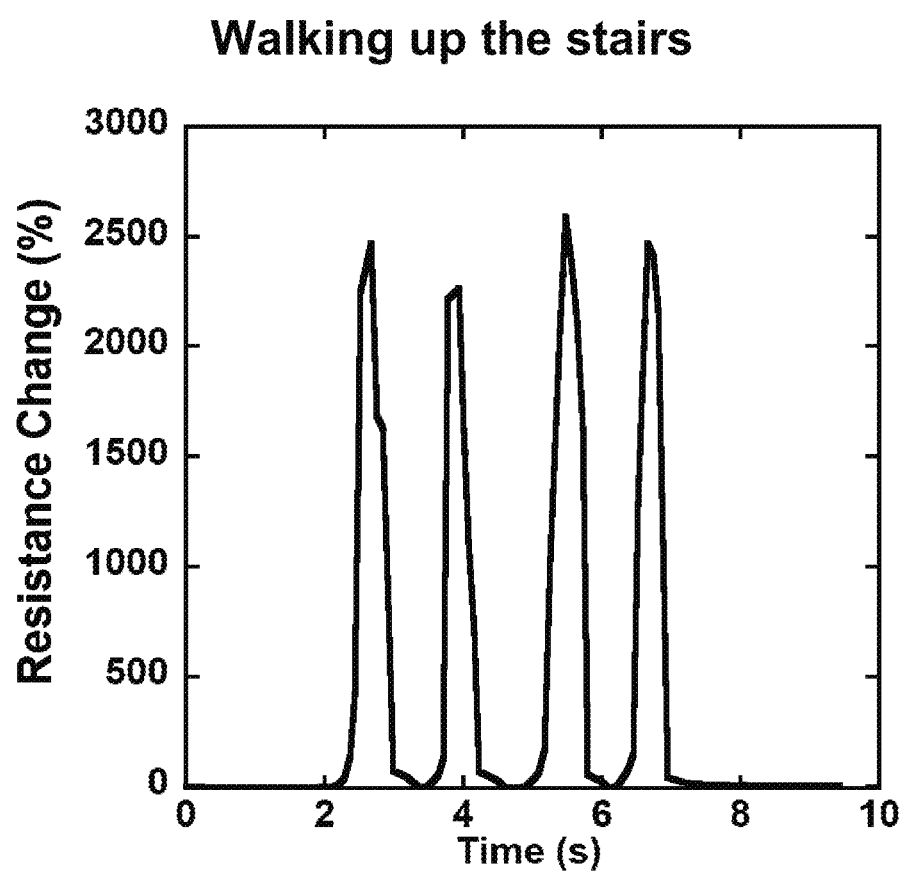

FIGS. 24A and 24B show the sensing response when walking on flat ground and walking up the stairs wearing the knee sleeve with the carbon nanotube sensor. When walking on flat ground, the knee is bent during each step, causing an increase of about 1300% in electrical resistance. While walking up the stairs, the resistance change is almost 2500% for each step as the knee is bent significantly more during the ascent. Due to the extremely high sensitivity of these wearable sensors, there are potential applications of these sensors for measuring the range of motion at joints. This is especially useful for a patient undergoing rehabilitation after injuries or joint replacement surgeries. Gait analysis is typically done in a laboratory setting using motion capture cameras. Not only is this technique expensive, but also time-consuming and complex, and the subject can be monitored only for a limited amount of time in a controlled setting. Using wearable sensors that can be integrated into clothing can be used for human motion analysis for extended periods and outside of a laboratory setting, in the patient's natural work or home environment and hence enabling accurate feedback and tracking of rehabilitation progress helping clinicians make an informed decision.

4.8 Detecting Minute Finger Movements

Figure 25A:
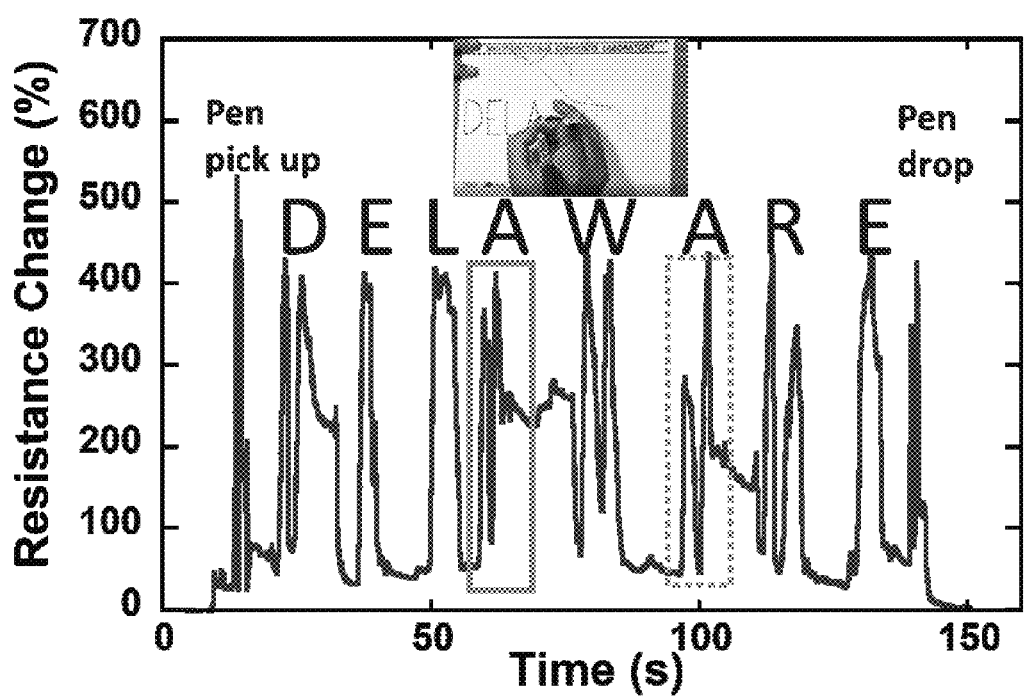
FIGS. 25A-25C: The sensor is integrated into a finger sleeve and worn on the index finger.
Figure 25B:
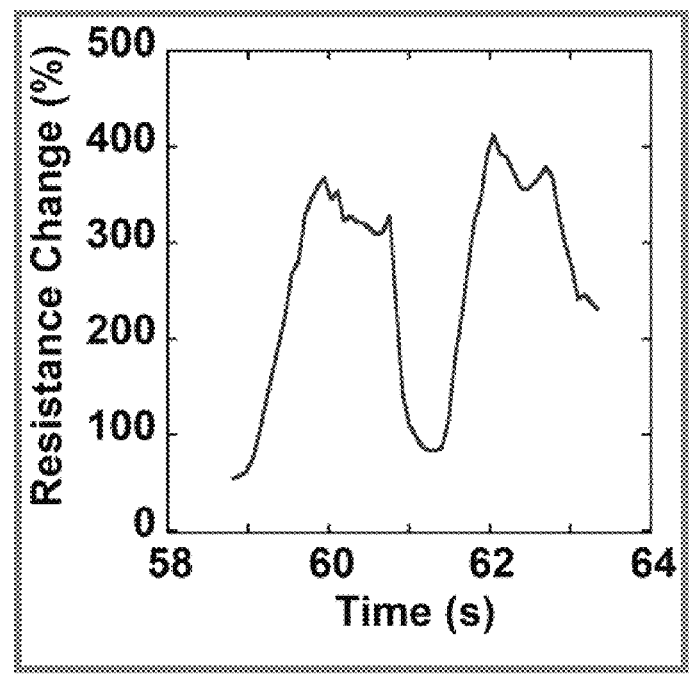
Figure 25C:
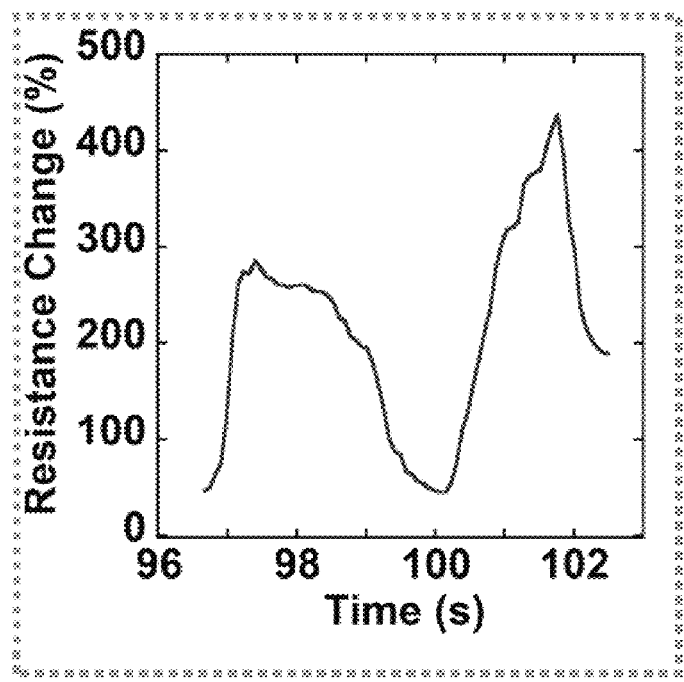

FIG. 25A shows the resistance response when the sensor is combined into a finger sleeve worn over the index finger, and the word 'DELAWARE' is written in capital letters using a pen. Due to the ultrahigh sensitivity of the carbon nanotube-based sensor, it can capture small movements of the finger when writing. Even limited movements to pick up the marker from the table and keeping it back after writing cause a resistance change of over 400%. FIGS. 25B and 25C show the sensing response for writing the letter 'A' in the word 'DELAWARE,' the $4^{th}$ and the $6^{th}$ letter. The resistance signature for both the letters 'A' is similar where the peaks are due to the finger movements to draw the two angled lines. This enables potential applications in gesture recognition, where often fingers are used to make signs.

Figure 26:
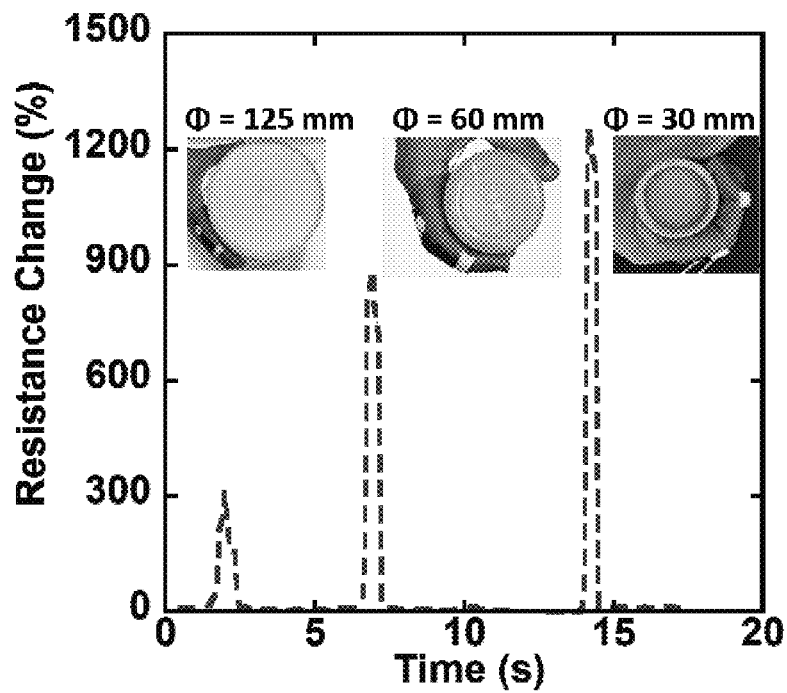
FIG. 26: Sensing response when an object of varying diameter is held in hand with the sensor integrated into a finger sleeve worn over the index finger. The smaller the object, the more the finger is bent, causing a higher change in electrical resistance.

FIG. 26 displays the resistance change when the index finger with the sensor integrated sleeve is bent to hold objects of different diameters. The smaller the diameter, the more is the finger bent, causing a more substantial change in electrical resistance. The sensor is so sensitive that it is also able to detect minuscule muscle contractions.

4.9 Ultrahigh Sensitivity to Detect Muscle Contractions

Figure 27:
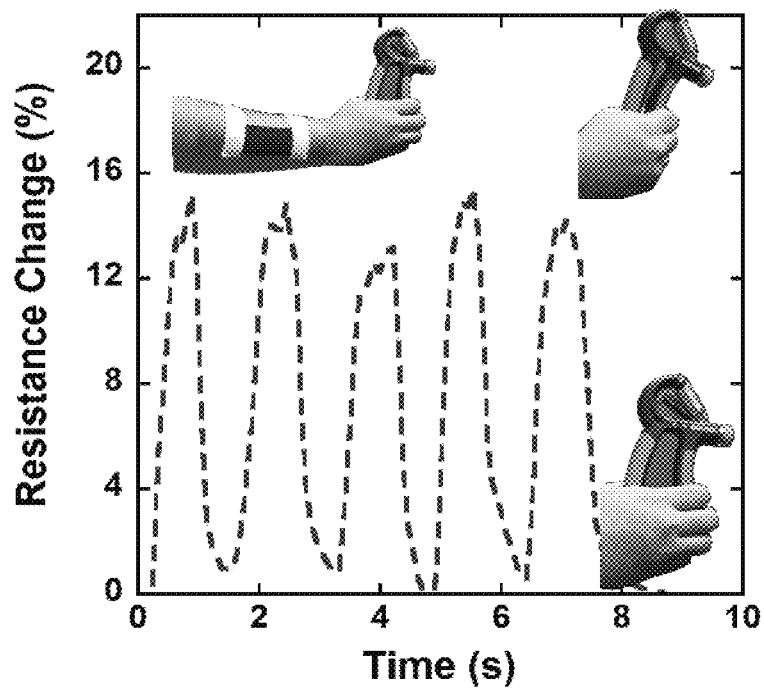
FIG. 27: Sensor worn over the forearm while using a wrist exercising device. When the device is compressed, the muscles are actuated, causing them to expand slightly, leading to a change in the resistance.

FIG. 27 shows the sleeve integrated with the sensor worn over the forearm while using a wrist exercising device. When the first is clinched to compress the spring-actuated wrist exercising device, the muscles in the forearms are activated, which causes them to expand. As a result, the electrical resistance of the sensor increases. This has promising applications in measuring the muscle actuation while performing activities or during rehabilitation in a non-invasive and comfortable manner.

SUMMARY AND CONCLUSIONS/INDUSTRIAL APPLICABILITY

A thin and flexible pressure sensor has been developed using a scalable and efficient electrophoretic deposition method to coat functionalized carbon nanotubes on a non-woven aramid fabric. An extremely wide range of pressure detection capability was demonstrated—in the tactile range to body weight and even higher. Preliminary experiments are conducted for gait analysis using these sensors attached to footwear, and the sensing response is validated using an instrumented treadmill. The flexible sensor is able to measure some of the important gait characteristics such as speed of walking and heel strikes. This novel sensor has potential applications in the field of prosthetics, e-skins for robots, human-machine interaction and creation of smart garments used for human performance monitoring.

Not only are the sensors able to detect different walking speeds, but they could also be potentially used for detecting gait imbalances in patients undergoing rehabilitation and track their improvement over time. Unlike the instrumented treadmill which gives an overall value of GRF, multiple sensors can be used to detect gait parameters such as heel strikes/toe strikes. The key advantages of using these sensors for gait analysis over an instrumented treadmill is the low cost and the ability to customize the footwear and sensor placement for every patient/athlete. More importantly, these sensors enable the gait measurement of subjects outside of the laboratory in their natural work or home environment. Measurements can be conducted over extended periods, unlike the instrumented treadmill where the clinician can monitor the subject for a limited amount of time.

In a second aspect of the invention, a dip-coating process was utilized to create a nanocomposite coating on the surfaces of the fiber in a knitted fabric to create a sensor that may be integrated into a garment for human motion analysis. The sensor response is characterized when subjected to axial extension and then integrated into a sleeve and tested for elbow joint motion, and the nanocomposite coating did not change the feel of the fabric, making it comfortable to wear. When subjected to axial tension, the sensor showed a reversible, non-linear response with electrical resistance changes over 150%. Ultra-high sensitivity is observed with elbow joint motion where the sensor electrical resistance change is over 3,000% in a fully flexed elbow. This high sensitivity compared to the response in tension is likely due to the multi-axial extension of the fabric around the elbow joint. These sensors, combined portable electronics, offer the potential to record real-time data on human motion outside of a laboratory environment.

In a third aspect, a flexible, lightweight, and comfortable to wear stretch sensor was developed by depositing carbon nanotubes on a knitted fabric using an innovative and scalable electrophoretic deposition method. The robustness of the coating due to the chemical bonding of the carbon nanotubes to the surface of the fibers ensures repeatable response when tested over multiple cycles. A resistance change of about 1200% is observed when the sensor is tested in tension to a strain of approximately 6% and when integrated into a knee-sleeve, a resistance change of over 3000% is measured. We envision that these textile-based wearable sensors with ultrahigh sensitivity can be used for detecting and analyzing human motion outside of the laboratory setting.

In a fourth aspect, a scalable and efficient electrophoretic deposition technique was used to create thin, uniform nanostructured carbon nanotube films on a variety of commonly used fibers or fabrics with different microstructures. The carbon nanotube coating is robustly bonded on the surface of the fibers. Flexible, stretchable, and breathable wearable sensors are created which are comfortable to wear and have extremely high sensitivity. These sensors can measure joint motion at elbow/knee or small finger movements or detect minute muscle contractions. When integrated into sleeves worn over the knee, an exceptional 3000% change in resistance is observed when the leg is bent to sit on a chair. Upon integrated into finger sleeves, the sensor demonstrates the ability to measure extremely small finger movements due to writing or bending of a finger. The capability to detect minuscule muscle movements due to exercising is demonstrated. The fabric-based, comfortable to wear sensors have the potential to revolutionize and stimulate growth in wide-ranging potential applications from analyzing human gait and measure the range of motion in an affordable and out-of-laboratory setting to gesture recognitions and functional garments for biomedical devices.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation".

It should be understood that the steps of the exemplary methods set forth herein are not necessarily required to be performed in the order described, and the order of the steps of such methods should be understood to be merely exemplary. Likewise, additional steps might be included in such methods, and certain steps might be omitted or combined, in methods consistent with various embodiments of the present invention.

As used in this application, the word "exemplary" is used herein to mean serving as an example, instance, or illustration. Any aspect or design described herein as "exemplary" is not necessarily to be construed as preferred or advantageous over other aspects or designs. Rather, use of the word "exemplary" is intended to present concepts in a concrete fashion.

An artisan of ordinary skill will appreciate that various modifications may be made to the invention herein described without departing from the scope or spirit of the invention as defined in the appended claims.

What is claimed is:

1. An article configured to be worn by a living being, comprising:
   (a) a piezoresistive sensor including:
      (i) a first stretchy fabric featuring fibers arranged as loops that are interconnected in at least two dimensions;
      (ii) a plurality of carbon nanotubes deposited on said fibers as to form a carbon nanotube-deposited first stretchy fabric and to render the carbon nanotube-deposited fabric electrically conductive; and
      (iii) at least two electrodes attached to said carbon nanotube-deposited fabric in a spaced-apart relationship, thereby defining a known electrical resistance therebetween;
   (b) a second stretchy fabric configured as a garment or portion thereof, said piezoresistive sensor being attached to said second stretchy fabric;
   (c) whereby a force or pressure applied to said piezoresistive sensor or to said second stretchy fabric causes a deformation of said piezoresistive sensor, which deformation is sensed as a change in said electrical resistance; and
   (d) said article being configured to be worn by the living being as said garment or portion of said garment.

2. The article of claim 1, wherein said garment or portion thereof includes a sleeve.

3. The article of claim 1, wherein said carbon nanotube deposit is on all or some of the fibers within the fabric.

4. The article of claim 1, wherein said carbon nanotubes are multi-walled and functionalized.

5. The article of claim 1, wherein said first stretchy fabric includes natural fibers including at least one of cotton and wool fibers.

6. The article of claim 1, wherein said first stretchy fabric includes synthetic fibers including at least one of nylon, polyester, glass, aramid and elastane fibers.

7. The article of claim 2, wherein said sleeve is configured to be worn on one of (i) a human arm and positioned at an elbow, (ii) a human leg and positioned at a knee, and (iii) a human finger.

8. The article of claim 2, wherein the piezoresistive sensor displays ultrahigh sensitivity, a resistance change in excess of 3000% when configured as an elbow or knee sleeve, worn on the elbow or knee and subject to complete flexion.

9. The article of claim 2, wherein said first stretchy fabric includes a weft-knitted fabric of nylon, polyester and elastane, and further wherein the piezoresistive sensor displays the extremely high sensitivity and the ability to detect minuscule body movements such as muscle contractions or breathing or neck movements.

10. The article of claim 1, wherein said fiber-based piezoresistive sensor is attached to said second stretchy fabric by at least one of stitching, gluing, heat fusing and heat bonding.

11. The article of claim 1, wherein said carbon nanotube-deposited first stretchy fabric furthermore is breathable.

* * * * *